US007968543B2

(12) United States Patent
James et al.

(10) Patent No.: US 7,968,543 B2
(45) Date of Patent: Jun. 28, 2011

(54) METHODS OF ADMINISTERING N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL} UREA TO TREAT PROLIFERATIVE DISEASE

(75) Inventors: Joyce K. James, San Diego, CA (US); Traci L. Savall, San Diego, CA (US); Shawn R. Eichelberger, San Diego, CA (US)

(73) Assignee: Ambit Biosciences Corporation, San Diego, CA (US)

( * ) Notice: Subject to any disclaimer, the term of this patent is extended or adjusted under 35 U.S.C. 154(b) by 281 days.

(21) Appl. No.: 12/267,321

(22) Filed: Nov. 7, 2008

(65) Prior Publication Data

US 2009/0123418 A1 May 14, 2009

Related U.S. Application Data

(60) Provisional application No. 61/002,583, filed on Nov. 8, 2007, provisional application No. 61/005,803, filed on Dec. 7, 2007, provisional application No. 61/098,676, filed on Sep. 19, 2008, provisional application No. 61/112,060, filed on Nov. 6, 2008.

(51) Int. Cl.
*A61K 31/535* (2006.01)
*A61K 31/41* (2006.01)
*A61K 31/42* (2006.01)

(52) U.S. Cl. ............ 514/231.5; 514/360; 514/380

(58) Field of Classification Search ............ 514/231.5, 514/360, 380
See application file for complete search history.

(56) References Cited

U.S. PATENT DOCUMENTS
2007/0232604 A1   10/2007   Bhagwat et al.

FOREIGN PATENT DOCUMENTS
WO   WO 2007/109120   9/2007

OTHER PUBLICATIONS

Gilliland et al., "The roles of FLT3 in hematopoiesis and leukemia," *Blood* 2002, vol. 100, pp. 1532-1542.
Stirewalt et al., "The role of FLT3 in haematopoietic malignancies," *Nat. Rev. Cancer* 2003, vol. 3, pp. 650-665.
Malempati et al., "Outcome after relapse among children with standard risk (SR) ALL treated on CCG-1952," *Blood (ASH Annual Annual Meeting Abstracts)*, 2004, vol. 104, Iss. 11, Abstract 520.
Levis et al., "FLT3 tyrosine kinase inhibitors," *Int .J. Hematol.* 2005, vol. 82, pp. 100-107.
Levis et al., "A FLT3-targeted tyrosine kinase inhibitor is cytotoxic to leukemia cells in vitro and in vivo," *Blood* 2002, vol. 99, pp. 3885-3891.
Kelly et al., "CT53518, a novel selective FLT3 antagonist for the treatment of acute myelogenous leukemia (AML)," *Cancer Cell* 2002, vol. 1, pp. 421-432.
Weisberg et al., "Inhibition of mutant FLT3 receptors in leukemia cells by the small molecule tyrosine kinase inhibitor PKC412," *Cancer Cell* 2002, vol. 1, pp. 433-443.
Yee et al., "SU5416 and SU5614 inhibit kinase activity of wild-type and mutant FLT3 receptor tyrosine kinase," *Blood* 2002, vol. 100, pp. 2941-2949.
Whartenby et al., "Inhibition of FLT3 signaling targets DCs to ameliorate autoimmune disease," *Proc. Natl. Acad. Sci. U.S.A.* 2005, vol. 102, pp. 16741-16746.
U.S. Appl. No. 60/994,635, filed Sep. 19, 2007, Bhagwat et al.
U.S. Appl. No. 12/233,906, filed Sep. 19, 2008, Bhagwat et al.

*Primary Examiner* — Raymond J Henley, III
(74) *Attorney, Agent, or Firm* — Jones Day

(57) ABSTRACT

Provided herein are methods of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, to human patients. Specifically, dosing, dosing schedules or dosing regimens are provided herein. Further, pharmaceutical formulations are provided. Methods of treating proliferative diseases or FLT-3 mediated diseases in humans are also provided.

45 Claims, 4 Drawing Sheets

METHODS OF ADMINISTERING N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL} UREA TO TREAT PROLIFERATIVE DISEASE

CROSS REFERENCE TO RELATED APPLICATIONS

This application claims the benefit of the priority of U.S. Provisional Application Nos. 61/002,583, filed Nov. 8, 2007; 61/005,803, filed Dec. 7, 2007; 61/098,676, Sep. 19, 2008; and 61/112,060, filed Nov. 6, 2008, the disclosure of each of which is incorporated herein by reference in its entirety.

FIELD

Provided herein are methods of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, to human patients. Specifically, dosing, dosing schedules or dosing regimens are provided herein. Further, pharmaceutical formulations are provided. Methods of treating proliferative diseases or FLT-3 mediated diseases in humans are also provided.

BACKGROUND

Fms-like tyrosine kinase 3 (FLT3), which is also known as FLK-2 (fetal liver kinase 2) and STK-1 (stem cell kinase 1), plays an important role in the proliferation and differentiation of hematopoietic stem cells. FLT3 receptor kinase is expressed in normal hematopoietic cells, placenta, gonads, and brain. However, this enzyme is expressed at very high levels on the cells of more than 80% of myelogenous patients and of a fraction of acute lymphoblastic leukemia cells. This enzyme can also be found on cells from patients with chronic myelogenous leukemia in lymphoid blast crisis.

It has been reported that FLT3 kinase is mutated in 30% of acute myeloid leukemia (AML) and in a subset of acute lymphoblastic leukemia (ALL) as well (Gilliland et al., *Blood* 2002, 100, 1532-1542; Stirewalt et al., *Nat. Rev. Cancer* 2003, 3, 650-665). The most common activating mutations in FLT3 are internal tandem duplications within the juxtamembrane region. The point mutations, insertions, or deletions in the kinase domain are less common. Some of these mutant FLT3 kinases are constitutively active. FLT3 mutations have been associated with a poor prognosis (Malempati et al., *Blood* 2004, 104, 11).

More than a dozen known FLT3 inhibitors are being developed and some have shown promising clinical effects against AML (Levis et al. *Int. J. Hematol.* 2005, 82, 100-107). It has been reported that some of small-molecule FLT3 inhibitors are effective in inducing apoptosis in cell lines with FLT3-activating mutations and prolonging survival of mice that express mutant FLT3 in their bone marrow cells (Levis et al., *Blood* 2002, 99, 3885-3891; Kelly et al., *Cancer Cell* 2002, 1, 421-432; Weisberg et al., *Cancer Cell* 2002, 1, 433-443; Yee et al., *Blood* 2002, 100, 2941-2949).

Despite the success in identification of small molecules that inhibit protein tyrosine kinases, there continues to be a need for a safe and effective method of using or administering such compounds, particularly to humans having AML and ALL, including compounds useful for the treatment of FLT-3 mediated diseases.

SUMMARY OF THE DISCLOSURE

In one embodiment, provided herein is a method for treating proliferative diseases by administering to a mammal having a proliferative disease at least 12 mg per day of a compound of Formula I:

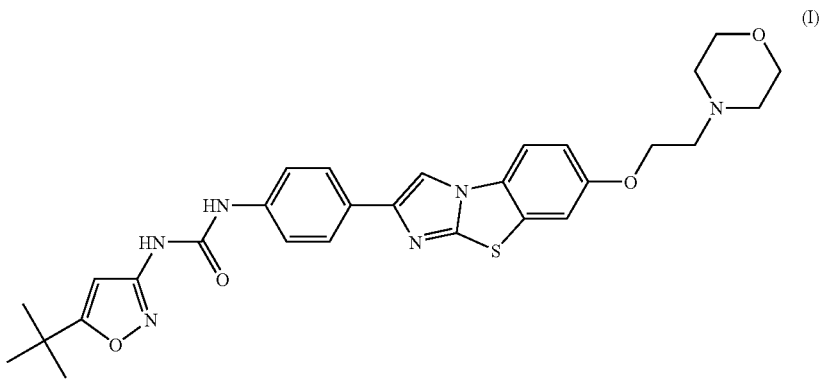

or a pharmaceutically acceptable salt or solvate thereof.

In another embodiment, provided herein is a method for treating proliferative diseases by administering to a mammal having a proliferative disease from about 0.1 to about 10 mg/kg/day of the compound of Formula I, or a pharmaceutically acceptable salt or solvate thereof.

In yet another embodiment, provided herein is a method for treating proliferative diseases by administering to a mammal having a proliferative disease the compound of Formula I, or a pharmaceutically acceptable salt or solvate thereof, in an amount that is sufficient to provide a plasma concentration of the compound at steady state, of about 0.01 to about 10 µM.

In yet another embodiment, provided herein is a method for treating proliferative diseases by administering to a mammal having a proliferative disease the compound of Formula I, or a pharmaceutically acceptable salt or solvate thereof, in an amount that is sufficient to provide a peak plasma concentration of the compound of about 0.01 to about 10 µM.

In still another embodiment, provided herein is a method for treating proliferative diseases by administering to a mammal having a proliferative disease the compound of Formula I, or a pharmaceutically acceptable salt or solvate thereof, in an amount that is sufficient to provide a trough plasma concentration of the compound of about 0.01 to about 10 µM when two or more doses of the compound are administered.

In one embodiment, the proliferative disease in the methods provided herein is cancer. In another embodiment, the proliferative disease in the methods provided herein is a solid tumor. In yet another embodiment, the proliferative disease in the methods provided herein is a blood-borne tumor. In yet another embodiment, the proliferative disease is a leukemia. In one embodiment, the leukemia is acute myelogenous leukemia. In another embodiment, the leukemia is acute lymphocytic leukemia. In still another embodiment, the leukemia is a drug resistant leukemia.

In one embodiment, the drug resistant leukemia is drug resistant acute myelogenous leukemia. In one embodiment, the mammal having the drug resistant acute myelogenous leukemia has an activating mutant FLT3. In still another embodiment, the drug resistant acute myelogenous leukemia is Philadelphia positive.

In another embodiment, the drug resistant leukemia is drug resistant acute lymphocytic leukemia. In one embodiment, the mammal having the drug resistant acute myelogenous leukemia has an activating mutant FLT3. In still another embodiment, the drug resistant acute myelogenous leukemia is Philadelphia positive.

Each method provided herein may further comprise administering a second therapeutic agent. In one embodiment, the second therapeutic agent is an anticancer agent. In one embodiment, the second therapeutic agent is a protein kinase inhibitor; in another embodiment, a tyrosine kinase inhibitor; and in yet another embodiment, a second FLT3 kinase inhibitor.

In another embodiment, provided herein are method of administering N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, to a human having a disease in the amount of about 27 to about 1000 mg per day in a continuous manner. In a further embodiment, 200, 450, or 675 mg per day is administrated continuously to a human having a disease. Moreover, in another embodiment, 40 mg per day to 675 mg per day of N-(5-tert-butyl-isoxazol-3-yl)-N'-{4-[7-(2-morpholin-4-yl-ethoxy)imidazo[2,1-b][1,3]benzothiazol-2-yl]phenyl}urea, or a pharmaceutically acceptable salt or solvate thereof, is administered to a human having AML to treat that disease.

DETAILED DESCRIPTION

Figure 1:
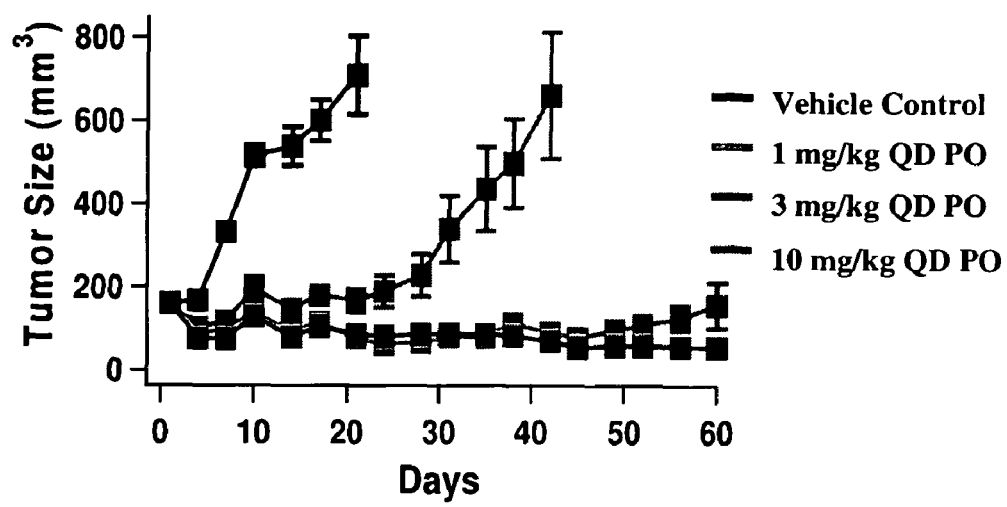
FIG. 1 shows effects of N-(5-tert-butyl-isoxazol-3-yl)-N'-{4-[7-(2-morpholin-4-yl-ethoxy)imidazo[2,1-b][1,3]benzothiazol-2-yl]phenyl}urea on tumor growth in a mouse xenograft model, in which the FLT3-dependent human leukemia cell line MV4-11 was implanted in the mice.

To facilitate understanding of the disclosure set forth herein, a number of terms are defined below.

The terms "FLT3-mediated diseases or disorders" shall include diseases associated with or implicating FLT3 activity, for example, the overactivity of FLT3, and conditions that accompany with these diseases. The term "overactivity of FLT3" refers to either 1) FLT3 expression in cells which normally do not express FLT3; 2) FLT3 expression by cells which normally do not express FLT3; 3) increased FLT3 expression leading to unwanted cell proliferation; or 4) mutations leading to constitutive activation of FLT3. Examples of "FLT3-mediated diseases or disorders" include disorders resulting from over stimulation of FLT3 or from abnormally high amount of FLT3 activity, due to abnormally high amount of FLT3 or mutations in FLT3. It is known that overactivity of FLT3 has been implicated in the pathogenesis of a number of diseases, including inflammatory and autoimmune diseases, cell proliferative disorders, neoplastic disorders and cancers as described herein.

The term "proliferative disorder or disease" refers to unwanted cell proliferation of one or more subset of cells in a multicellular organism resulting in harm (i.e., discomfort or decreased life expectancy) to the multicellular organisms. A proliferative disorder or disease can occur in different types of animals and humans. For example, as used herein, "proliferative disorder or disease" includes neoplastic disorders and other proliferative disorders.

The term "neoplastic disorder or disease" or "cancer" refers to a tumor resulting from abnormal or uncontrolled cellular growth. Examples of neoplastic disorders include, but are not limited to, hematopoietic disorders, such as the myeloproliferative disorders, thrombocythemia, essential thrombocytosis (ET), angiogenic myeloid metaplasia, myelofibrosis (MF), myelofibrosis with myeloid metaplasia (MMM), chronic idiopathic myelofibrosis (IMF), polycythemia vera (PV), the cytopenias, and pre-malignant myelodysplastic syndromes; cancers, such as glioma cancers, lung cancers, breast cancers, colorectal cancers, prostate cancers, gastric cancers, esophageal cancers, colon cancers, pancreatic cancers, ovarian cancers, and hematologic malignancies.

The term "hematologic malignancy" refers to cancer of the body's blood-forming and immune system-the bone marrow and lymphatic tissue. Examples of hematological malignancies include, for instance, myelodysplasia, lymphomas, leukemias, lymphomas (non-Hodgkin's lymphoma), Hodgkin's disease (also called Hodgkin's lymphoma), and myeloma, such as acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma, (MM).

The term "leukemia" refers to malignant neoplasms of the blood-forming tissues, including, but not limited to, chronic lymphocytic leukemia, chronic myelocytic leukemia, acute lymphoblastic leukemia, acute myelogenous leukemia and acute myeloblastic leukemia. The leukemia can be relapsed, refractory, or resistant to conventional therapy.

The term "promyelocytic leukemia" or "acute promyelocytic leukemia" refers to a malignancy of the bone marrow in which there is a deficiency of mature blood cells in the myeloid line of cells and an excess of immature cells called promyelocytes. It is usually marked by an exchange of parts of chromosomes 15 and 17.

The term "acute lymphocytic leukemia," "acute lymphoblastic leukemia," or "ALL" refers to a malignant disease caused by the abnormal growth and development of early nongranular white blood cell or lymphocytes.

The term "T-cell leukemia" refers to a disease in which certain cells of the lymphoid system called T lymphocytes or T cells are malignant. T cells are white blood cells that normally can attack virus-infected cells, foreign cells, and cancer cells; and produce substances that regulate the immune response.

The term "relapsed" refers to a situation where a subject or a mammal, which has had a remission of cancer after therapy has a return of cancer cells.

The term "refractory or resistant" refers to a circumstance where a subject or a mammal, even after intensive treatment, has residual cancer cells in his body.

The term "anticancer agent" is meant to include anti-proliferative agents and chemotherapeutic agents, including, but not limited to, antimetabolites (e.g., 5-fluoro uracil, methotrexate, fludarabine, cytarabine (also known as cytosine arabinoside or Ara-C), and HDAC (high dose cytarabine)), antimicrotubule agents (e.g., vinca alkaloids, such as vincristine and vinblastine; and taxanes, such as paclitaxel and docetaxel), alkylating agents (e.g., mechlorethamine, chlorambucil, cyclophosphamide, melphalan, melphalan, ifosfamide, carmustine, azacitidine, decitibine, busulfan, cyclophosphamide, dacarbazine, ifosfamide, and nitrosoureas, such as carmustine, lomustine, bischloroethylnitrosurea, and hydroxyurea), platinum agents (e.g., cisplatin, carboplatin, oxaliplatin, satraplatin (JM-216), and CI-973), anthracyclines (e.g., doxorubicin and daunorubicin), antitumor antibiotics (e.g., mitomycin, bleomycin, idarubicin, adriamycin, daunomycin (also known as daunorubicin, rubidomycin, or cerubidine), and mitoxantrone), topoisomerase inhibitors (e.g., etoposide and camptothecins), purine anatagonists or pyrimidine antagonists (e.g., 6-mercaptopurine, 5-fluorouracil, cytarabile, clofarabine, and gemcitabine), cell maturing agents (e.g., arsenic trioxide and tretinoin), DNA repair enzyme inhibitors (e.g., podophyllotoxines, etoposide, irinotecan, topotecan, and teniposide), enzymes that prevent cell survival (e.g., asparaginase and pegaspargase), histone deacetylase inhibitors (e.g., vorinostat), any other cytotoxic agents (e.g., estramustine phosphate, dexamethasone, prednimustine, and procarbazine), hormones (e.g., dexamethasone, prednisone, methylprednisolone, tamoxifen, leuprolide, flutamide, and megestrol), monocolonal antibodies (e.g., gemtuzumab ozogamicin, alemtuzumab, rituximab, and yttrium-90-ibritumomab tiuxetan), immunomodulators (e.g., thalidomide and lenalidomide), Bcr-Abl kinase inhibitors (e.g., AP23464, AZD0530, CGP76030, PD180970, SKI-606, imatinib, BMS354825 (dasatinib), AMN107 (nilotinib), and VX-680), hormone agonists or antagonists, partial agonists or partial antagonists, kinase inhibitors, surgery, radiotherapy (e.g., gamma-radiation, neutron bean radiotherapy, electron beam radiotherapy, proton therapy, brachytherapy, and systemic radioactive isotopes), endocrine therapy, biological response modifiers (e.g., interferons, interleukins, and tumor necrosis factor), hyperthermia and cryotherapy, and agents to attenuate any adverse effects (e.g., antiemetics).

The term "subject" refers to an animal, including, but not limited to, a mammal, including a primate (e.g., human), cow, sheep, goat, horse, dog, cat, rabbit, rat, or mouse. The terms "subject" and "patient" are used interchangeably herein in reference, for example, to a mammalian subject, such as a human subject.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disease; or reducing a subject's risk of acquiring a disorder, disease, or condition.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, excipient, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition; Lippincott Williams & Wilkins: Philadelphia, Pa., 2005; *Handbook of Pharmaceutical Excipients,* 5th Edition; Rowe et al., Eds., The Pharmaceutical Press and the American Pharmaceutical Association: 2005; and *Handbook of Pharmaceutical Additives,* 3rd Edition; Ash and Ash Eds., Gower Publishing Company: 2007; *Pharmaceutical Preformulation and Formulation,* Gibson Ed., CRC Press LLC: Boca Raton, Fla., 2004).

The term "drug resistance" refers to the condition when a disease does not respond to the treatment of a drug or drugs. Drug resistance can be either intrinsic, which means the disease has never been responsive to the drug or drugs, or it can be acquired, which means the disease ceases responding to a drug or drugs that the disease had previously responded to. In certain embodiments, drug resistance is intrinsic. In certain embodiments, the drug resistance is acquired. As used herein, the term "drug resistance" is meant to include imatinib-resistance, dasatinib-resistance, and/or nilotinib-resistance.

The term "hydrate" means a compound provided herein or a salt thereof, which further includes a stoichiometric or non-stoichiometric amount of water bound by non-covalent intermolecular forces.

The term "solvate" means a solvate formed from the association of one or more solvent molecules to a compound provided herein. The term "solvate" includes hydrates (e.g., mono-hydrate, dihydrate, trihydrate, tetrahydrate and the like).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The Compound

The compound suitable for use in the methods provided herein is N-(5-tert-butyl-isoxazol-3-yl)-N'-{4-[7-(2-morpholin-4-yl-ethoxy)imidazo[2,1-b][1,3]benzothiazol-2-yl]phenyl}urea, having the structure of Formula I:

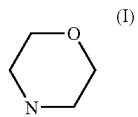

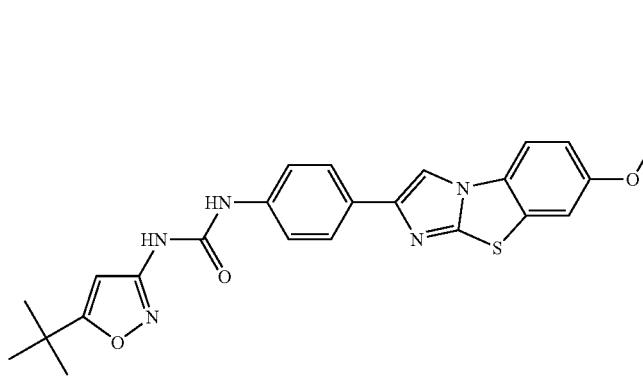

or a pharmaceutically acceptable salt or solvate thereof.

The compound of Formula I can be prepared according to the methods described in U.S. patent application Ser. No. 11/724,992, filed Mar. 16, 2007, published as U.S. Pub. No. 2007/0232604 on Oct. 4, 2007, the entirety of which is incorporated by reference herein. The compound can be also synthesized according to other methods apparent to those of skill in the art based upon the teaching herein.

In one embodiment, the compound used in the methods provided herein is a free base of the compound of Formula I, or a pharmaceutically acceptable solvate thereof. In one embodiment, the free base is a solid. In another embodiment, the free base is a solid in an amorphous form. In yet another embodiment, the free base is a solid in a crystalline form. The compound of Formula I in solid forms can be prepared according to the method described in U.S. Provisional Patent App. Ser. No. 60/994,635, filed Sep. 19, 2007, the entirety of which is incorporated by reference herein; or using other methods known in the art.

In another embodiment, the free base is a pharmaceutically acceptable solvate. In one embodiment, the free base is a hydrate. In another embodiment, the pharmaceutically acceptable solvent is a methanol solvate. The methanol solvate of the compound of Formula I can be prepared according to the method described in U.S. Provisional Patent App. Ser. No. 60/994,635, filed Sep. 19, 2007; or using other methods known in the art.

In yet another embodiment, the compound used in the methods provided herein is a pharmaceutically acceptable salt of the compound of Formula I, which includes, but is not limited to, acetate, adipate, alginate, aspartate, benzoate, benzenesulfonate(besylate), bisulfate, butyrate, citrate, camphorate, camphorsulfonate, cyclopentanepropionate, digluconate, dodecylsulfate, 1,2-ethanedisulfonate(edisylate), ethanesulfonate(esylate), formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate(mesylate), 2-naphthalenesulfonate(napsylate), nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate, or undecanoate salts.

In one embodiment, the pharmaceutically acceptable salt is a hydrochloride, hydrobromide, sulfate, mesylate, esylate, edisylate, besylate, tosylate, or napsylate salt of the compound of Formula I. In another embodiment, the pharmaceutically acceptable salt is a hydrochloride salt of the compound of Formula I. In yet another embodiment, the pharmaceutically acceptable salt is a hydrobromide of the compound of Formula I. In yet another embodiment, the pharmaceutically acceptable salt is a sulfate of the compound of Formula I. In yet another embodiment, the pharmaceutically acceptable salt is a mesylate of the compound of Formula I. In yet another embodiment, the pharmaceutically acceptable salt is an esylate of the compound of Formula I. In yet another embodiment, the pharmaceutically acceptable salt is an edisylate of the compound of Formula I. In yet another embodiment, the pharmaceutically acceptable salt is a besylate of the compound of Formula I. In yet another embodiment, the pharmaceutically acceptable salt is a tosylate of the compound of Formula I. In still another embodiment, the pharmaceutically acceptable salt is a napsylate of the compound of Formula I. The pharmaceutically acceptable salt of the compound of Formula I can be prepared according to the method described in U.S. Provisional Patent App. Ser. No. 60/994,635, filed Sep. 19, 2007; or patent application Ser. No. 12/233,906, filed Sep. 19, 2008; each of which is incorporated herein by reference in its entirety. The pharmaceutically acceptable salt of the compound of Formula I can also be prepared using other methods known in the art.

As used herein, the compound of Formula I is intended to encompass all possible stereoisomers, unless a particular stereochemistry is specified. Where structural isomers of the compound of Formula I are interconvertible via a low energy barrier, the compound of Formula I may exist as a single tautomer or a mixture of tautomers. This can take the form of proton tautomerism in the compound that contains, e.g., a urea group; or so-called valence tautomerism in the compound that contain an aromatic moiety.

Pharmaceutical Compositions

In one embodiment, provided herein are pharmaceutical compositions, which comprise the compound of Formula I, or a pharmaceutically acceptable salt or solvate thereof, as an active ingredient, in combination with one or more pharmaceutically acceptable carriers. In one embodiment, the pharmaceutical composition comprises at least one nonrelease controlling excipients or carriers. In another embodiment, the pharmaceutical composition comprises at least one release controlling and at least one nonrelease controlling excipients or carriers.

In another embodiment, provided herein are pharmaceutical compositions, which comprise the compound of Formula I, or a pharmaceutically acceptable salt or solvate thereof, as an active ingredient, in combination with one or more pharmaceutically acceptable carriers, each of which is selected from the group consisting of hydroxypropyl-β-cyclodextrin, mannitol, sodium starch glycolate (EXPLOTAB®), citric acid, PEG400, PEG6000, polyvinylpyrrolidone (PVP), lauroyl polyoxylglycerides (GELUCIRE® 44/14, Gattefosse Corp., Paramus, N.J.), PLURONIC® F68, silicone dioxide, and water. PLURONIC® F68 (also known as Poloxamer 188) is a block copolymer of ethylene oxide and propylene oxide.

In yet another embodiment, provided herein is a pharmaceutical composition which comprises the compound of Formula I, or a pharmaceutically acceptable salt or solvate thereof, and hydroxypropyl-β-cyclodextrin (HPBCD). In certain embodiments, the HPBCD-containing composition is formulated as an aqueous solution, which is obtained by adding an aqueous HPBCD solution at a desired concentration to the appropriate amount of the compound of Formula I, or a pharmaceutically acceptable salt or solvate thereof, to achieve a desired final concentration of the compound, including, but not limited to, final concentrations of about 1, about 2, about 3, about 5, about 10, about 15, about 50, or about 100 mg/mL. In one embodiment, the HPBCD composition contains about 5% HPBCD. In another embodiment, the HPBCD composition contains about 22% HPBCD. In certain embodiments, the pharmaceutical composition contains 2, 3, or 5 mg/mL of a compound of Formula I, or a pharmaceutically acceptable salt or solvate thereof, in 5% HPBCD. In certain embodiments, the pharmaceutical composition contains 1, 3, or 10 mg/mL of a compound of Formula I, or a pharmaceutically acceptable salt or solvate thereof, in 22% HPBCD.

Exemplary pharmaceutical compositions are shown in Table 1.

TABLE 1

| Component | Formulation Ia (2 mg/mL Preparation) | Formulation Ib (5 mg/mL Preparation) |
| --- | --- | --- |
| A compound of Formula I in vial (mg) | 50 mg | 50 mg |
| HPBCD (5% stock, freshly prepared) | 25 mL | 10 mL |

In yet another embodiment, provided herein is a pharmaceutical composition for reconstitution with an aqueous solution that comprises one or more pharmaceutically acceptable carriers, prior to administration. In one embodiment, the pharmaceutical composition comprises the compound of Formula I, or a pharmaceutically acceptable salt or solvate thereof. In another embodiment, the pharmaceutical composition comprises the compound of Formula I in a vial. In yet another embodiment, the pharmaceutical composition comprises from about 1 to about 200 mg, from about 10 to about 100 mg, or from about 10 to 60 mg, or 10 mg, 12 mg, 14 mg, 16 mg, 18 mg, 20 mg, 25 mg, 27 mg, 30 mg, 35 mg, 40 mg, 45 mg, 50 mg, 55 mg, or 60 mg of the compound, or a pharmaceutically acceptable salt or solvate thereof. In one embodiment, the aqueous solution used for reconstitution comprises HPBCD. In certain embodiments, the aqueous solution comprises 5% by weight of HPBCD. In certain embodiments, the aqueous solution comprises 22% by weight of HPBCD.

In yet another embodiment, provided herein is a pharmaceutical composition, which comprises the compound of Formula I, or a pharmaceutically acceptable salt or solvate thereof, in combination with PEG 400 and water. In certain embodiments, the ratio between PEG400 and water is 3 to 1.

In yet another embodiment, provided herein is a pharmaceutical composition, which comprises the compound of Formula I, or a pharmaceutically acceptable salt or solvate thereof, in combination with mannitol and EXPLOTAB®. In certain embodiments, the pharmaceutical composition is formulated as capsules. Exemplary pharmaceutical compositions are shown in Table 2.

TABLE 2

| Component | Formulation IIa | Formulation IIb |
| --- | --- | --- |
| A compound of Formula I | 75 mg | 25 mg |
| Mannitol | 282 mg | 332 mg |
| EXPLOTAB ® | 22.8 mg | 22.8 mg |

In yet another embodiment, provided herein is a pharmaceutical composition, which comprises the compound of Formula I, or a pharmaceutically acceptable salt or solvate thereof, in combination with mannitol, EXPLOTAB®, and citric acid. In certain embodiments, the pharmaceutical composition is formulated as capsules. In certain embodiments, the compound of Formula I, or a pharmaceutically acceptable salt or solvate thereof, is micronized, e.g., using jet-mill. Exemplary pharmaceutical compositions are shown in Table 3.

TABLE 3

| Component | Formulation IIIa | Formulation IIIb |
| --- | --- | --- |
| A compound of Formula I | 75 mg | 25 mg |
| Mannitol | 206 mg | 309 mg |
| EXPLOTAB ® | 22.8 mg | 22.8 mg |
| Citric acid | 76 mg | 25 mg |

In yet another embodiment, provided herein is a pharmaceutical composition, which comprises the compound of Formula I, or a pharmaceutically acceptable salt or solvate thereof, in combination with PEG6000, mannitol, and EXPLOTAB®. In certain embodiments, the pharmaceutical composition is formulated as capsules. Exemplary pharmaceutical compositions are shown in Table 4.

TABLE 4

| Component | Formulation IVa | Formulation IVb |
| --- | --- | --- |
| A compound of Formula I | 50 mg | 30 mg |
| PEG6000 | 113 mg (31%) | 70.5 mg (18.8%) |
| Mannitol | 158 mg (43.3%) | 229.5 mg (61.2%) |
| EXPLOTAB ® | 44 (12%) | 45 mg (12%) |

In yet another embodiment, provided herein is a pharmaceutical composition, which comprises the compound of Formula I, or a pharmaceutically acceptable salt or solvate thereof, in combination with polyvinylpyrrolidone (PVP), mannitol, and EXPLOTAB®. In certain embodiments, the pharmaceutical composition is formulated as capsules. Exemplary pharmaceutical compositions are shown in Table 5.

TABLE 5

| Component | Formulation Va | Formulation Vb |
|---|---|---|
| A compound of Formula I | 75 mg | 25 mg |
| Mannitol | 226 mg | 276 mg |
| PVP | 14 mg | 14 mg |
| EXPLOTAB ® | 35 mg | 35 mg |

In yet another embodiment, provided herein is a pharmaceutical composition, which comprises the compound of Formula I, or a pharmaceutically acceptable salt or solvate thereof, in combination with GELUCIRE®. In certain embodiments, the pharmaceutical composition is formulated as capsules. In certain embodiment, the pharmaceutical composition comprises a dihydrochloride of N-(5-tert-butyl-isoxazol-3-yl)-N'-{4-[7-(2-morpholin-4-yl-ethoxy)imidazo[2,1-b][1,3]benzothiazol-2-yl]phenyl}urea and GELUCIRE® 44/14. An exemplary pharmaceutical composition is shown in Table 6.

TABLE 6

| Component | Formulation VI |
|---|---|
| A compound of Formula I | 50 mg |
| GELUCIRE ® | 470 mg |

In yet another embodiment, provided herein is a pharmaceutical composition, which comprises the compound of Formula I, or a pharmaceutically acceptable salt or solvate thereof, in combination with GELUCIRE® and PEG6000. In certain embodiments, the pharmaceutical composition is formulated as capsules. In certain embodiments, the pharmaceutical composition comprises three parts by weight of GELUCIRE® and one parts by weight of PEG6000.

In yet another embodiment, provided herein is a pharmaceutical composition, which comprises the compound of Formula I, or a pharmaceutically acceptable salt or solvate thereof, in combination with mannitol, EXPLOTAB®, and PLURONIC® F68. In certain embodiments, the pharmaceutical composition is formulated as capsules. An exemplary pharmaceutical composition is shown in Table 7.

TABLE 7

| Component | Formulation VII |
|---|---|
| A compound of Formula I | 75 mg |
| Mannitol | 275.5 mg |
| EXPLOTAB ® | 22.8 mg |
| PLURONIC ® F68 | 11.4 mg |

In yet another embodiment, provided herein is a pharmaceutical composition, which comprises the compound of Formula I, or a pharmaceutically acceptable salt or solvate thereof, in combination with GELUCIRE®, PEG6000, silicone dioxide, mannitol, and EXPLOTAB®. In certain embodiments, the pharmaceutical composition is formulated as capsules. An exemplary pharmaceutical composition is shown in Table 8.

TABLE 8

| Component | Formulation VIII |
|---|---|
| A compound of Formula I | 60 mg |
| GELUCIRE ® | 37.5 mg |
| PEG 6000 | 112.5 mg |
| Silicone dioxide | 10 mg |
| Mannitol | 117.5 |
| EXPLOTAB ® | 37.5 mg |

In yet another embodiment, provided herein is a pharmaceutical composition, which comprises the compound of Formula I, or a pharmaceutically acceptable salt or solvate thereof, in combination with HPBCD, mannitol, and EXPLOTAB®. In certain embodiments, the pharmaceutical composition is formulated as capsules. An exemplary pharmaceutical composition is shown in Table 9.

TABLE 9

| Component | Formulation IX |
|---|---|
| Compound of Formula I | 70 mg |
| HPBCD | 140 mg |
| Mannitol | 119 mg |
| EXPLOTAB ® | 21 mg |

In still another embodiment, provided herein is a pharmaceutical composition, which comprises the compound of Formula I, or a pharmaceutically acceptable salt or solvate thereof, in combination with HPBCD. In certain embodiments, the pharmaceutical composition is formulated as lyophilized powder. In certain embodiments, the compound of Formula I used in the pharmaceutical composition is a cocrystal of the compound of Formula I, or a pharmaceutically acceptable salt or solvate thereof, and HPBCD. As used here, the term "cocrystal" refers to a crystal containing two or more distinct molecular components within the crystal lattice (unit cell). An exemplary pharmaceutical composition is shown in Table 10.

TABLE 10

| Component | Formulation Xa | Formulation Xb | Formulation Xc |
|---|---|---|---|
| Compound of Formula I | 10 mg | 10 mg | 75 mg |
| HPBCD | 110 mg | 50 mg | 75 mg |

In certain embodiments, the pharmaceutical compositions provided herein are formulated in a dosage from about 1 to about 100 mg, or from about 1 to about 60 mg, or from about 10 to about 60 mg, from about 10 to about 40 mg, from about 10 to about 27 mg, or from about 10 to about 25 mg of the compound of Formula I, or a pharmaceutically acceptable salt or solvate thereof.

In certain embodiments, the compound of Formula I used in the pharmaceutical compositions provided herein is in a solid form. Suitable solid forms include, but are not limited to, solid forms comprising the free base of the compound of Formula I, and solid forms comprising salts of the compound of Formula I, including, but not limited to, HCl salts, HBr salts, sulfate salts, mesylate salts, esylate salts, edisylate salts, besylate salts, tosylate salts, and napsylate salts. In certain embodiments, the HCl salts of the compound of Formula I include mono-HCl salts and bis-HCl salts. In certain embodiments, solid forms provided herein include polymorphs, solvates (including hydrates), and cocrystals comprising the compound of Formula I and/or salts thereof. In certain embodiments, the solid form is a cocrystal of the compound of Formula I, or a pharmaceutically acceptable salt or solvate thereof, and HPBCD. In certain embodiments, the compound of Formula I used in the pharmaceutical compositions provided herein is a dihydrochloride salt of N-(5-tert-butyl-isoxazol-3-yl)-N'-{4-[7-(2-morpholin-4-yl-ethoxy)imidazo[2,1-b][1,3]benzothiazol-2-yl]phenyl}urea. Some of these solid forms are described in U.S. Provisional App. Ser. No. 60/994,635, filed Sep. 19, 2007; patent application Ser. No. 12/233,906, filed Sep. 19, 2008; each of which is incorporated herein by reference in its entirety.

The pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

The pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

Further to these discussed above, the pharmaceutical compositions provided herein may be provided in solid, semi-solid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG) (e.g., PEG400 and PEG6000); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica (silicone dioxide) or silica gels, such as AEROSIL® 200 (W.R. Grace Co., Baltimore, Md.) and CAB-O-

SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (e.g., TWEEN® 20), poloxamers (e.g., PLURONIC® F68), polyoxyethylene sorbitan monooleate 80 (e.g., TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, polyvinylpyrrolidone, and lauroyl polyoxylglycerides (e.g., GELUCIRE® 44/14). Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of non-aqueous liquids utilized in emulsions include mineral oil and cottonseed oil. Organic acids include citric and tartaric acid. Sources of carbon dioxide include sodium bicarbonate and sodium carbonate.

Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

Methods of Use

In one embodiment, provided herein is a method for treating a proliferative disease in a mammal, which comprises administering to the mammal having the proliferative disease a therapeutically effective amount of the compound of Formula I, or a pharmaceutically acceptable salt or solvate thereof. In certain embodiment, the therapeutically effective amount is a range from about 0.1 to about 1,000 mg per day, from about 0.1 to about 500 mg per day, from about 0.1 to about 450 mg per day, from about 0.1 to about 300 mg per day, from about 0.1 to about 200 mg per day, from about 1 to about 100 mg per day, from about 5 to about 100 mg per day, from about 10 to about 90 mg per day, from about 10 to about 80 mg per day, from about 10 to about 70 mg per day, from about 15 to about 65 mg per day, or from about 20 to about 60 mg per day. In one embodiment, the therapeutically effective amount is from about 0.1 to about 1,000 mg per day. In another embodiment, the therapeutically effective amount is from about 0.1 to about 500 mg per day. In yet another embodiment, the therapeutically effective amount is from about 0.1 to about 450 mg per day. In yet another embodiment, the therapeutically effective amount is from about 0.1 to about 400 mg per day. In yet another embodiment, the therapeutically effective amount is from about 0.1 to about 200 mg per day. In yet another embodiment, the therapeutically effective amount is from about 1 to about 100 mg per day. In yet another embodiment, the therapeutically effective amount is from about 5 to about 100 mg per day. In yet another embodiment, the therapeutically effective amount is from about 10 to about 90 mg per day. In yet another embodiment, the therapeutically effective amount is from about 10 to about 80 mg per day. In yet another embodiment, the therapeutically effective amount is from about 10 to about 70 mg per day. In yet another embodiment, the therapeutically effective amount is from about 15 to about 65 mg per day. In still another embodiment, the therapeutically effective amount is from about 20 to about 60 mg per day.

In certain embodiments, the therapeutically effective amount is about 12, about 18, about 20, about 25, about 27, about 30, about 35, about 40, about 45, about 50, about 55, about 60, about 90, about 135, about 200, about 300, or about 450 mg per day. In one embodiment, the therapeutically effective amount is about 12 mg per day. In another embodiment, the therapeutically effective amount is about 18 mg per day. In yet another embodiment, the therapeutically effective amount is about 20 mg per day. In yet another embodiment, the therapeutically effective amount is about 25 mg per day. In yet another embodiment, the therapeutically effective amount is about 27 mg per day. In yet another embodiment, the therapeutically effective amount is about 30 mg per day. In yet another embodiment, the therapeutically effective amount is about 35 mg per day. In yet another embodiment, the therapeutically effective amount is about 40 mg per day. In yet another embodiment, the therapeutically effective amount is about 45 mg per day. In yet another embodiment, the therapeutically effective amount is about 50 mg per day. In yet another embodiment, the therapeutically effective amount is about 55 mg per day. In yet another embodiment, the therapeutically effective amount is about 60 mg per day. In yet another embodiment, the therapeutically effective amount is about 90 mg per day. In yet another embodiment, the therapeutically effective amount is about 135 mg per day. In yet another embodiment, the therapeutically effective amount is about 200 mg per day. In yet another embodiment, the therapeutically effective amount is about 300 mg per day. In still another embodiment, the therapeutically effective amount is about 450 mg per day.

In another embodiment, provided herein is a method for treating a proliferative disease in a mammal, which comprises administering to the mammal having the proliferative disease a therapeutically effective amount of the compound of Formula I, or a pharmaceutically acceptable salt or solvate thereof. In certain embodiment, the therapeutically effective amount is a range from about 0.01 to about 20 mg/kg/day, from about 0.01 to about 15 mg/kg/day, from about 0.01 to about 10 mg/kg/day, from about 0.01 to about 9 mg/kg/day, from about 0.01 to about 8 mg/kg/day, from about 0.01 to about 7 mg/kg/day, from about 0.01 to about 6 mg/kg/day, from about 0.01 to about 5 mg/kg/day, from about 0.01 to about 5 mg/kg/day, from about 0.05 to about 5 mg/kg/day, from about 0.05 to about 4 mg/kg/day, from about 0.1 to about 3 mg/kg/day, from about 0.1 to about 2 mg/kg/day, from about 0.1 to about 1 mg/kg/day, or from about 0.24 mg/kg/day to about 9 mg/kg/day.

In one embodiment, the therapeutically effective amount is from about 0.01 to about 20 mg/kg/day. In another embodiment, the therapeutically effective amount is from about 0.01 to about 15 mg/kg/day. In yet another embodiment, the therapeutically effective amount is from about 0.01 to about 10 mg/kg/day. In yet another embodiment, the therapeutically effective amount is from about 0.01 to about 9 mg/kg/day. In yet another embodiment, the therapeutically effective amount is from about 0.01 to about 8 mg/kg/day. In yet another embodiment, the therapeutically effective amount is from about 0.01 to about 7 mg/kg/day. In yet another embodiment, the therapeutically effective amount is from about 0.01 to about 6 mg/kg/day. In yet another embodiment, the therapeutically effective amount is from about 0.01 to about 5 mg/kg/day. In yet another embodiment, the therapeutically effective amount is from about 0.05 to about 5 mg/kg/day. In yet another embodiment, the therapeutically effective amount is from about 0.05 to about 4 mg/kg/day. In yet another embodiment, the therapeutically effective amount is from about 0.1 to about 3 mg/kg/day. In yet another embodiment, the therapeutically effective amount is from about 0.1 to about 2 mg/kg/day. In yet another embodiment, the therapeutically effective amount is from about 0.1 to about 1 mg/kg/day. In still another embodiment, the therapeutically effective amount is from about 0.24 to about 9 mg/kg/day.

The administered dose can also be expressed in units other than as mg/kg/day. For example, doses for parenteral administration can be expressed as mg/m$^2$/day. One of ordinary skill in the art would readily know how to convert doses from mg/kg/day to mg/m$^2$/day to given either the height or weight of a subject or both (see, www.fda.gov/cder/cancer/animalframe.htm). For example, a dose of 1 mg/kg/day for a 65 kg human is approximately equal to 38 mg/m$^2$/day.

In yet another embodiment, provided herein is a method of treating a proliferative disease in a mammal, which comprises administering to the mammal having the proliferative disease a therapeutically effective amount of the compound of Formula I, or a pharmaceutically acceptable salt or solvate thereof, wherein the amount of the compound administered is sufficient to provide a plasma concentration of the compound at steady state, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.005 to about 0.5 µM, from about 0.01 to about 0.2 µM, or from about 0.01 to about 0.1 µM. In one embodiment, the amount of the compound administered is sufficient to provide a plasma concentration at steady state, of about 0.005 to about 100 µM. In another embodiment, the amount of the compound administered is sufficient to provide a plasma concentration at steady state, of about 0.005 to about 10 µM. In yet another embodiment, the amount of the compound administered is sufficient to provide a plasma concentration at steady state, of about 0.01 to about 10 µM. In yet another embodiment, the amount of the compound administered is sufficient to provide a plasma concentration at steady state, of about 0.01 to about 5 µM. In yet another embodiment, the amount of the compound administered is sufficient to provide a plasma concentration at steady state, of about 0.005 to about 1 µM. In yet another embodiment, the amount of the compound administered is sufficient to provide a plasma concentration at steady state, of about 0.005 to about 0.5 µM. In yet another embodiment, the amount of the compound administered is sufficient to provide a plasma concentration of the compound at steady state, of about 0.01 to about 0.2 µM. In still another embodiment, the amount of the compound administered is sufficient to provide a plasma concentration of the compound at steady state, of about 0.01 to about 0.1 µM. As used herein, the term "plasma concentration at steady state" is the concentration reached after a period of administration of a compound. Once steady state is reached, there are minor peaks and troughs on the time dependent curve of the plasma concentration of the compound.

In yet another embodiment, provided herein is a method of treating a proliferative disease in a mammal, which comprises administering to the mammal having the proliferative disease a therapeutically effective amount of the compound of Formula I, or a pharmaceutically acceptable salt, or solvate thereof, wherein the amount administered is sufficient to provide a maximum plasma concentration (peak concentration) of the compound, ranging from about 0.005 to about 100 µM, from about 0.005 to about 10 µM, from about 0.01 to about 10 µM, from about 0.01 to about 5 µM, from about 0.005 to about 1 µM, from about 0.005 to about 0.5 µM, from about 0.01 to about 0.2 µM, or from about 0.01 to about 0.1 µM. In one embodiment, the amount of the compound administered is sufficient to provide a maximum plasma concentration of the compound of about 0.005 to about 100 µM. In another embodiment, the amount of the compound administered is sufficient to provide a maximum plasma concentration of the compound of about 0.005 to about 10 µM. In yet another embodiment, the amount of the compound administered is sufficient to provide a maximum plasma concentration of the compound of about 0.01 to about 10 µM. In yet another embodiment, the amount of the compound administered is sufficient to provide a maximum plasma concentration of the compound of about 0.01 to about 5 µM. In yet another embodiment, the amount of the compound administered is sufficient to provide a maximum plasma concentration of the compound of about 0.005 to about 1 µM. In yet another embodiment, the amount of the compound administered is sufficient to provide a maximum plasma concentration of the compound of about 0.005 to about 0.5 µM. In yet another embodiment, the amount of the compound administered is sufficient to provide a maximum plasma concentration of the compound of about 0.01 to about 0.2 µM. In still another embodiment, the amount of the compound administered is sufficient to provide a maximum plasma concentration of the compound of about 0.01 to about 0.1 μM.

In yet another embodiment, provided herein is a method of treating a proliferative disease in a mammal, which comprises administering to the mammal having the proliferative disease a therapeutically effective amount of the compound of Formula I, or a pharmaceutically acceptable salt, or solvate thereof, wherein the amount administered is sufficient to provide a minimum plasma concentration (trough concentration) of the compound, ranging from about 0.005 to about 100 μM, from about 0.005 to about 10 μM, from about 0.01 to about 10 μM, from about 0.01 to about 5 μM, from about 0.005 to about 1 μM, about 0.005 to about 0.5 μM, from about 0.01 to about 0.2 μM, or from about 0.01 to about 0.1 μM, when more than one doses are administered. In one embodiment, the amount of the compound administered is sufficient to provide a minimum plasma concentration of the compound of about 0.005 to about 100 μM. In another embodiment, the amount of the compound administered is sufficient to provide a minimum plasma concentration of the compound of about 0.005 to about 10 μM. In yet another embodiment, the amount of the compound administered is sufficient to provide a minimum plasma concentration of the compound of about 0.01 to about 10 μM. In yet another embodiment, the amount of the compound administered is sufficient to provide a minimum plasma concentration of the compound of about 0.01 to about 5 μM. In yet another embodiment, the amount of the compound administered is sufficient to provide a minimum plasma concentration of the compound of about 0.005 to about 1 μM. In yet another embodiment, the amount of the compound administered is sufficient to provide a minimum plasma concentration of the compound of about 0.005 to about 0.5 μM. In yet another embodiment, the amount of the compound administered is sufficient to provide a minimum plasma concentration of the compound of about 0.01 to about 0.2 μM. In still another embodiment, the amount of the compound administered is sufficient to provide a minimum plasma concentration of the compound of about 0.01 to about 0.1 μM.

In still another embodiment, provided herein is a method of treating a proliferative disease in a mammal, which comprises administering to the mammal having the proliferative disease a therapeutically effective amount of the compound of Formula I, or a pharmaceutically acceptable salt, or solvate thereof, wherein the amount administered is sufficient to provide an area under the curve (AUC) of the compound, ranging from about 100 to about 50,000 ng*hr/mL, from about 100 to 25,000 ng*hr/mL, or from about 10,000 to 25,000 ng*hr/mL.

In certain embodiments, the mammal is a human.

In one embodiment, the proliferative disease is cancer. In another embodiment, the cancer is a leukemia.

In one embodiment, the leukemia is chronic lymphocytic leukemia, chronic myelocytic leukemia, acute lymphoblastic leukemia, acute myelogenous leukemia, and acute myeloblastic leukemia.

In another embodiment, the leukemia is acute leukemia. In one embodiment, the acute leukemia is acute myelogenous leukemia (AML). In one embodiment, acute myelogenous leukemia is undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the acute myelogenous leukemia is undifferentiated AML (M0). In yet another embodiment, the acute myelogenous leukemia is myeloblastic leukemia (M1). In yet another embodiment, the acute myelogenous leukemia is myeloblastic leukemia (M2). In yet another embodiment, the acute myelogenous leukemia is promyelocytic leukemia (M3 or M3 variant [M3V]). In yet another embodiment, the acute myelogenous leukemia is myelomonocytic leukemia (M4 or M4 variant with eosinophilia [M4E]). In yet another embodiment, the acute myelogenous leukemia is monocytic leukemia (M5). In yet another embodiment, the acute myelogenous leukemia is erythroleukemia (M6). In yet another embodiment, the acute myelogenous leukemia is megakaryoblastic leukemia (M7). In yet another embodiment, the acute myelogenous leukemia is promyelocytic leukemia. In yet another embodiment, the leukemia is attributable to a FLT3 internal tandem duplication (ITD) mutation. In yet another embodiment, the leukemia is attributable to a FLT3 point mutation. In still another embodiment, the FLT3 point mutation is a point mutation at amino acid D835.

In another embodiment, the acute leukemia is acute lymphocytic leukemia (ALL). In one embodiment, the acute lymphocytic leukemia is leukemia that originates in the blast cells of the bone marrow (B-cells), thymus (T-cells), or lymph nodes. The acute lymphocytic leukemia is categorized according to the French-American-British (FAB) Morphological Classification Scheme as L1—Mature-appearing lymphoblasts (T-cells or pre-B-cells), L2—Immature and pleomorphic (variously shaped) lymphoblasts (T-cells or pre-B-cells), and L3—Lymphoblasts (B-cells; Burkitt's cells). In another embodiment, the acute lymphocytic leukemia originates in the blast cells of the bone marrow (B-cells). In yet another embodiment, the acute lymphocytic leukemia originates in the thymus (T-cells). In yet another embodiment, the acute lymphocytic leukemia originates in the lymph nodes. In yet another embodiment, the acute lymphocytic leukemia is L1 type characterized by mature-appearing lymphoblasts (T-cells or pre-B-cells). In yet another embodiment, the acute lymphocytic leukemia is L2 type characterized by immature and pleomorphic (variously shaped) lymphoblasts (T-cells or pre-B-cells). In yet another embodiment, the acute lymphocytic leukemia is L3 type characterized by lymphoblasts (B-cells; Burkitt's cells).

In yet another embodiment, the leukemia is T-cell leukemia. In one embodiment, the T-cell leukemia is peripheral T-cell leukemia, T-cell lymphoblastic leukemia, cutaneous T-cell leukemia, and adult T-cell leukemia. In another embodiment, the T-cell leukemia is peripheral T-cell leukemia. In yet another embodiment, the T-cell leukemia is T-cell lymphoblastic leukemia. In yet another embodiment, the T-cell leukemia is cutaneous T-cell leukemia. In still another embodiment, the T-cell leukemia is adult T-cell leukemia.

In yet another embodiment, the leukemia is Philadelphia positive. In one embodiment, the Philadelphia positive leukemia is Philadelphia positive AML, including, but not limited to, undifferentiated AML (M0), myeloblastic leukemia (M1), myeloblastic leukemia (M2), promyelocytic leukemia (M3 or M3 variant [M3V]), myelomonocytic leukemia (M4 or M4 variant with eosinophilia [M4E]), monocytic leukemia (M5), erythroleukemia (M6), or megakaryoblastic leukemia (M7). In another embodiment, the Philadelphia positive leukemia is Philadelphia positive ALL.

In still another embodiment, the leukemia is drug resistant. In one embodiment, the subject has developed drug resistance to the anticancer therapy. In another embodiment, the subject has developed drug resistance to a FLT3 kinase inhibitor. In yet another embodiment, the subject has been treated with PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, or CHIR-258. In still another embodiment, the subject has a constitutively activating FLT3 mutant.

In certain embodiments, the cancer that can be treated with the methods provided herein includes, but is not limited to, bladder cancer, breast cancer, cervical cancer, colon cancer (e.g., colorectal cancer), esophageal cancer, head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer.

In certain embodiment, the cancer is a metastatic cancer, including, but not limited to, bladder cancer, breast cancer, cervical cancer, colon cancer (e.g., colorectal cancer), esophageal cancer, head and neck cancer, liver cancer, lung cancer (e.g., small cell and non-small cell lung cancers), melanoma, myeloma, neuroblastoma, ovarian cancer, pancreatic cancer, prostate cancer, renal cancer, sarcoma (e.g., osteosarcoma), skin cancer (e.g., squamous cell carcinoma), stomach cancer, testicular cancer, thyroid cancer, and uterine cancer. In one embodiment, the metastatic cancer is breast or prostate cancer. In another embodiment, the metastatic cancer is breast cancer. In yet another embodiment, the metastatic cancer is prostate cancer.

In certain embodiments, the mammal to be treated with one of the methods provided herein has not been treated with anticancer therapy prior to the administration of the compound of Formula I, or a pharmaceutically acceptable salt or solvate thereof. In certain embodiments, the mammal to be treated with one of the methods provided herein has been treated with anticancer therapy prior to the administration of the compound of Formula I, or a pharmaceutically acceptable salt or solvate thereof. In certain embodiments, the mammal to be treated with one of the methods provided herein has been treated with a FLT3 kinase inhibitor. In certain embodiments, the mammal to be treated with one of the methods provided herein has been treated with PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, CHIR-258, or others known or approved therapeutic agents for treating AML or ALL. In certain embodiments, the mammal to be treated with one of the methods provided herein has developed drug resistance to the anticancer therapy. In certain embodiments, the mammal to be treated with one of the methods provided herein has developed drug resistance to a FLT3 kinase inhibitor. In certain embodiments, the mammal to be treated with the methods provided herein has a constitutively activating FLT3 mutant.

The methods provided herein encompass treating a subject regardless of patient's age, although some diseases or disorders are more common in certain age groups. Further provided herein is a method for treating a subject who has undergone surgery in an attempt to treat the disease or condition at issue, as well as the one who have not. Because the subjects with cancer have heterogeneous clinical manifestations and varying clinical outcomes, the treatment given to a particular subject may vary, depending on his/her prognosis. The skilled clinician will be able to readily determine without undue experimentation, specific secondary agents, types of surgery, and types of non-drug based standard therapy that can be effectively used to treat an individual subject with cancer.

Depending on the disease to be treated and the subject's condition, the compound of Formula I, or a pharmaceutically acceptable salt or solvate thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. The compound of Formula I, or a pharmaceutically acceptable salt or solvate thereof, may be formulated, alone or together, in suitable dosage unit with pharmaceutically acceptable excipients, carriers, adjuvants and vehicles, appropriate for each route of administration. In one embodiment, the compound of Formula I, or a pharmaceutically acceptable salt or solvate thereof, is administered orally. In another embodiment, the compound of Formula I, or a pharmaceutically acceptable salt or solvate thereof, is administered parenterally. In yet another embodiment, the compound of Formula I, or a pharmaceutically acceptable salt or solvate thereof, is administered intravenously.

The compound of Formula I, or a pharmaceutically acceptable salt or solvate thereof can be delivered as a single dose such as, e.g., a single bolus injection, or oral tablets or pills; or over time such as, e.g., continuous infusion over time or divided bolus doses over time. The compound can be administered repetitively if necessary, for example, until the patient experiences stable disease or regression, or until the patient experiences disease progression or unacceptable toxicity. For example, stable disease for solid tumors generally means that the perpendicular diameter of measurable lesions has not increased by 25% or more from the last measurement. Response Evaluation Criteria in Solid Tumors (RECIST) Guidelines, *Journal of the National Cancer Institute* 92(3): 205-216 (2000). Stable disease or lack thereof is determined by methods known in the art such as evaluation of patient symptoms, physical examination, visualization of the tumor that has been imaged using X-ray, CAT, PET, or MRI scan and other commonly accepted evaluation modalities.

The compound of Formula I, or a pharmaceutically acceptable salt or solvate thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest that is no drug). As used herein, the term "daily" is intended to mean that a therapeutic compound, such as the compound of Formula I, is administered once or more than once each day, for example, for a period of time. The term "continuous" is intended to mean that a therapeutic compound, such as the compound of Formula I, is administered daily for an uninterrupted period of at least 10 days to 52 weeks. The term "intermittent" or "intermittently" as used herein is intended to mean stopping and starting at either regular or irregular intervals. For example, intermittent administration of the compound of Formula I is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as the compound of Formula I, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, the compound of Formula I, or a pharmaceutically acceptable salt or solvate thereof, is administered once a day. In another embodiment, The compound of Formula I, or a pharmaceutically acceptable salt or solvate thereof, is administered twice a day. In yet another embodiment, The compound of Formula I, or a pharmaceutically acceptable salt or solvate thereof, is administered three times a day. In still another embodiment, The compound of Formula I, or a pharmaceutically acceptable salt or solvate thereof, is administered four times a day.

In certain embodiments, the compound of Formula I, or a pharmaceutically acceptable salt or solvate thereof, is administered once per day from one day to six months, from one week to three months, from one week to four weeks, from one week to three weeks, or from one week to two weeks. In certain embodiments, the compound of Formula I, or a pharmaceutically acceptable salt or solvate thereof, is administered once per day for one week, two weeks, three weeks, or four weeks. In one embodiment, the compound of Formula I, or a pharmaceutically acceptable salt or solvate thereof, is administered once per day for one week. In another embodiment, the compound of Formula I, or a pharmaceutically acceptable salt or solvate thereof, is administered once per day for two weeks. In yet another embodiment, the compound of Formula I, or a pharmaceutically acceptable salt or solvate thereof, is administered once per day for three weeks. In still another embodiment, the compound of Formula I, or a pharmaceutically acceptable salt or solvate thereof, is administered once per day for four weeks.

In certain embodiments, the compound of Formula I, or a pharmaceutically acceptable salt or solvate thereof, is administered once per day for about 1 week, 2 weeks, 3 weeks, about 4 weeks, about 6 weeks, about 9 weeks, about 12 weeks, about 15 weeks, about 18 weeks, about 21 weeks, or about 26 weeks. In certain embodiments, the compound of Formula I is administered intermittently. In certain embodiments, the compound of Formula I is administered intermittently in the amount of from about 40 to 450 mg per day. In certain embodiments, the compound of Formula I is administered continuously. In certain embodiments, the compound of Formula I is administered continuously in the amount ranging from about 12 mg to 1000 mg per day. In certain embodiments, the compound of Formula I is administered continuously in the amount ranging from about 12 mg to 2000 mg per day, or from about 27 mg to 1000 mg per day. In certain embodiments, the compound of Formula I is administered continuously in the amount ranging from about 200 mg to 1000 mg per day. In certain embodiments, the compound of Formula I is administered continuously in the amount ranging from about 200 mg to 675 mg per day. In certain embodiments, The compound of Formula I is administered continuously in the amount ranging from about 200 mg to 450 mg per day. In certain embodiments, the compound of Formula I is administered continuously for 28 days. In certain embodiments, the compound of Formula I is administered continuously in the amount of about 200 mg. In certain embodiments, the compound of Formula I is administered continuously in the amount of about 450 mg. In certain embodiments, the compound of Formula I is administered continuously in the amount of about 675 mg. In certain embodiments, the compound of Formula I is administered continuously in the amount of about 1000 mg.

In certain embodiments, the compound of Formula I, or a pharmaceutically acceptable salt or solvate thereof, is cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one embodiment, the compound of Formula I, or a pharmaceutically acceptable salt or solvate thereof, is administered daily in a single or divided doses for one week, two weeks, three weeks, four weeks, five weeks, six weeks, eight weeks, ten weeks, fifteen weeks, or twenty weeks, followed by a rest period of about 1 day to about ten weeks. For example, the methods contemplate using cycling of one week, two weeks, three weeks, four weeks, five weeks, six weeks, eight weeks, ten weeks, fifteen weeks, or twenty weeks. In another embodiment, the compound of Formula I, or a pharmaceutically acceptable salt or solvate thereof, is administered daily in a single or divided doses for one week, two weeks, three weeks, four weeks, five weeks, or six weeks with a rest period of 1, 3, 5, 7, 9, 12, 14, 16, 18, 20, 22, 24, 26, 28, 29, or 30 days. In some embodiments, the rest period is 14 days. In some embodiments, the rest period is 28 days. In one embodiment, the rest period is a period that is sufficient for bone marrow recovery. The frequency, number and length of dosing cycles can be increased or decreased.

In certain embodiments, the methods provided herein comprise: i) administering to the mammal at a first daily dose of the compound of Formula I, or a pharmaceutically acceptable salt or solvate thereof; ii) resting for a period of at least one day where the compound of Formula I is not administered to the mammal; iii) administering a second dose of the compound to the mammal; and iv) repeating steps ii) to iii) a plurality of times. In certain embodiments, the first daily dose is from about 0.1 mg/kg to about 10 mg/kg. In certain embodiments, the second daily dose is from about 0.1 mg/kg to about 10 mg/kg. In certain embodiments, the first daily dose is higher than the second daily dose. In certain embodiments, the second daily dose is higher than the first daily dose.

In certain embodiments, the rest period is 2 days, 3 days, 5 days, 7 days, 10 days, 12 days, 13 days, 14 days, 15 days, 17 days, 21 days, or 28 days. In one embodiment, the rest period is at least 2 days and steps ii) through iii) are repeated at least three times. In another embodiment, the rest period is at least 2 days and steps ii) through iii) are repeated at least five times. In yet another embodiment, the rest period is at least 3 days and steps ii) through iii) are repeated at least three times. In yet another embodiment, the rest period is at least 3 days and steps ii) through iii) are repeated at least five times. In yet another embodiment, the rest period is at least 7 days and steps ii) through iii) are repeated at least three times. In yet another embodiment, the rest period is at least 7 days and steps ii) through iii) are repeated at least five times. In yet another embodiment, the rest period is at least 14 days and steps ii) through iii) are repeated at least three times. In yet another embodiment, the rest period is at least 14 days and steps ii) through iii) are repeated at least five times. In yet another embodiment, the rest period is at least 21 days and steps ii) through iii) are repeated at least three times. In yet another embodiment, the rest period is at least 21 days and steps ii) through iii) are repeated at least five times. In yet another embodiment, the rest period is at least 28 days and steps ii) through iii) are repeated at least three times. In still another embodiment, the rest period is at least 28 days and steps ii) through iii) are repeated at least five times.

In certain embodiments, the compound of Formula I, or a pharmaceutically acceptable salt or solvate thereof, is administered continuously to a patient. In certain embodiments, the compound of Formula I, or a pharmaceutically acceptable salt or solvate thereof, is administered continuously to a patient in the amount from about 0.1 to about 1,000 mg per day, from about 1 to about 675 mg per day, from about 1 to about 500 mg per day, from about 12 to about 450 mg per day, from about 12 to about 300 mg per day, from about 12 to about 200 mg per day, from about 12 to about 100 mg per day, from about 12 to about 100 mg per day, from about 12 to about 90 mg per day, from about 12 to about 80 mg per day, from about 12 to about 70 mg per day, from about 18 to about 65 mg per day, or from about 18 to about 60 mg per day. In certain embodiments, the compound of Formula I, or a pharmaceutically acceptable salt or solvate thereof, is administered continuously to a patient in the amount of about 12, about 18, about 20, about 25, about 27, about 30, about 35, about 40, about 45, about 50, about 55, about 60, about 90, about 135, about 200, about 300, about 450, or about 675 mg per day. It is understood that the duration of the treatment may vary with the age, weight, and condition of the patient being treated, and may be determined empirically using known testing protocols or according to the professional judgment of the person providing or supervising the treatment. In certain embodiments, the compound of Formula I, or a pharmaceutically acceptable salt or solvate thereof, is administered continuously for about 1 to about 52 weeks. In certain embodiments, the compound of Formula I, or a pharmaceutically acceptable salt or solvate thereof, is administered continuously for about 1, 2, 3, 4, 5, 6, 7, 8, 9, 10, 11, or 12 months. In certain embodiments, the compound of Formula I, or a pharmaceutically acceptable salt or solvate thereof, is administered continuously for about 14, about 28, about 42, about 84, or about 112 days.

In each embodiment provided herein, the method may further comprise a diagnostic step for determining the presence of a constitutively activating FLT3 mutant in a mammal.

The compound of Formula I can also be combined or used in combination with other therapeutic agents useful in the treatment and/or prevention of a disease described herein.

As used herein, the term "in combination" includes the use of more than one therapy (e.g., one or more prophylactic and/or therapeutic agents). However, the use of the term "in combination" does not restrict the order in which therapies (e.g., prophylactic and/or therapeutic agents) are administered to a subject with a disease or disorder. A first therapy (e.g., a prophylactic or therapeutic agent such as a compound provided herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent) to the subject. Triple therapy is also contemplated herein.

The route of administration of the compound of Formula I is independent of the route of administration of a second therapy. In one embodiment, the compound of Formula I is administered orally. In another embodiment, the compound of Formula I is administered intravenously. Thus, in accordance with these embodiments, the compound of Formula I is administered orally or intravenously, and the second therapy can be administered orally, parenterally, intraperitoneally, intravenously, intraarterially, transdermally, sublingually, intramuscularly, rectally, transbuccally, intranasally, liposomally, via inhalation, vaginally, intraoccularly, via local delivery by catheter or stent, subcutaneously, intraadiposally, intraarticularly, intrathecally, or in a slow release dosage form. In one embodiment, the compound of Formula I and a second therapy are administered by the same mode of administration, orally or by IV. In another embodiment, the compound of Formula I is administered by one mode of administration, e.g., by IV, whereas the second agent (an anticancer agent) is administered by another mode of administration, e.g., orally.

In certain embodiments, each method provided herein may independently, further comprise the step of administering a second therapeutic agent. In one embodiment, the second therapeutic agent is an anticancer agent. In another embodiment, the anticancer agent is an antimetabolite, including, but not limited to, 5-fluoro uracil, methotrexate, cytarabine (also known as cytosine arabinoside or Ara-C), and HDAC (high dose cytarabine) and fludarabine. In yet another embodiment, the anticancer agent is an antimicrotubule agent, including, but not limited to, vinca alkaloids (e.g., vincristine and vinblastine) and taxanes (e.g., paclitaxel and docetaxel). In yet another embodiment, the anticancer agent is an alkylating agent, including, but not limited to, cyclophosphamide, melphalan, carmustine, and nitrosoureas (e.g., bischloroethylnitrosurea and hydroxyurea). In yet another embodiment, the anticancer agent is a platinum agent, including, but not limited to, cisplatin, carboplatin, oxaliplatin, satraplatin (JM-216), and CI-973. In yet another embodiment, the anticancer agent is an anthracycline, including, but not limited to, doxrubicin and daunorubicin. In yet another embodiment, the anticancer agent is an antitumor antibiotic, including, but not limited to, mitomycin, idarubicin, adriamycin, and daunomycin (also known as daunorubicin). In yet another embodiment, the anticancer agent is a topoisomerase inhibitor, e.g., etoposide and camptothecins. In yet another embodiment, the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

In another embodiment, the anticancer agent is a Bcr-Abl kinase inhibitor. In one embodiment, the Bcr-Abl kinase inhibitor is selected from the group consisting of imatinib, BMS354825 (dasatinib), AMN107 (nilotinib), AP23464, AZD0530, CGP76030, ON012380, INN-0406 (NS-187), SKI-606 (bosutinib), VX-680, and pyrrolo[2,3-d]pyrimidines including PD166326, PD173955 and PD180970. In another embodiment, the Bcr-Abl kinase inhibitor is imatinib. In yet another embodiment, the Bcr-Abl kinase inhibitor is dasatinib. In yet another embodiment, the Bcr-Abl kinase inhibitor is nilotinib. In yet another embodiment, the Bcr-Abl kinase inhibitor is AP23464. In yet another embodiment, the Bcr-Abl kinase inhibitor is AZD0530. In yet another embodiment, the Bcr-Abl kinase inhibitor is CGP76030. In yet another embodiment, the Bcr-Abl kinase inhibitor is SKI-606. In yet another embodiment, the Bcr-Abl kinase inhibitor is ON012380. In yet another embodiment, the Bcr-Abl kinase inhibitor is INN-0406 (NS-187). In yet another embodiment, the Bcr-Abl kinase inhibitor is a pyrrolo[2,3-d]pyrimidine. In another embodiment, the Bcr-Abl kinase inhibitor is VX-680. In another embodiment, the Bcr-Abl kinase inhibitor is PD166326. In yet another embodiment, the Bcr-Abl kinase inhibitor is PD173955. In still another embodiment, the Bcr-Abl kinase inhibitor is PD180970.

In still another embodiment, the anticancer agent is a FLT3 kinase inhibitor. In one embodiment, the FLT3 kinase inhibitor is selected from the group consisting of PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, and CHIR-258. In another embodiment, the FLT3 kinase inhibitor is PKC 412. In yet another embodiment, the FLT3 kinase inhibitor is MLN 578. In yet another embodiment, the FLT3 kinase inhibitor is CEP-701. In yet another embodiment, the FLT3 kinase inhibitor is CT 53518. In yet another embodiment, the FLT3 kinase inhibitor is CT-53608. In yet another embodiment, the FLT3 kinase inhibitor is CT-52923. In yet another embodiment, the FLT3 kinase inhibitor is D-64406. In yet another embodiment, the FLT3 kinase inhibitor is D-65476. In yet another embodiment, the FLT3 kinase inhibitor is AGL-2033. In yet another embodiment, the FLT3 kinase inhibitor is AG1295. In yet another embodiment, the FLT3 kinase inhibitor is AG1296. In yet another embodiment, the FLT3 kinase inhibitor is KN-1022. In yet another embodiment, the FLT3 kinase inhibitor is KN-1022. In yet another embodiment, the FLT3 kinase inhibitor is SU5416. In yet another embodiment, the FLT3 kinase inhibitor is SU5614. In yet another embodiment, the FLT3 kinase inhibitor is SU11248. In yet another embodiment, the FLT3 kinase inhibitor is L-00021649. In still another embodiment, the FLT3 kinase inhibitor is CHIR-258.

Other therapies or anticancer agents that may be used in combination with the compound of Formula I include surgery, radiotherapy (e.g., gamma-radiation, neutron beam radiotherapy, electron beam radiotherapy, proton therapy, brachytherapy, and systemic radioactive isotopes), endocrine therapy, biologic response modifiers (e.g., interferons, interleukins, and tumor necrosis factor (TNF)), hyperthermia and cryotherapy, agents to attenuate any adverse effects (e.g., antiemetics), and other approved chemotherapeutic drugs, including, but not limited to, alkylating drugs (mechlorethamine, chlorambucil, cyclophosphamide, melphalan, and ifosfamide), antimetabolites (cytarabine (also known as cytosine arabinoside or Ara-C), HDAC (high dose cytarabine), and methotrexate), purine antagonists and pyrimidine antagonists (6-mercaptopurine, 5-fluorouracil, cytarbine, and gemcitabine), spindle poisons (vinblastine, vincristine, vinorelbine, and paclitaxel), podophyllotoxins (etoposide, irinotecan, and topotecan), antibiotics (daunorubicin, doxorubicin, bleomycin, and mitomycin), nitrosoureas (carmustine and lomustine), inorganic ions (cisplatin and carboplatin), enzymes (asparaginase), and hormones (tamoxifen, leuprolide, flutamide, and megestrol), imatinib, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

EXAMPLES

Example 1

Evaluation of Cellular Proliferation Assay in FLT3-Dependent vs. Independent Cell Lines Cancer cell viability and proliferation can be evaluated using a tetrazolium salt reduction cell-based assay. In viable cells, this colorimetric assay can measure mitochondrial reduction of a tetrazolium component (MTS) into an insoluble formazan product. MV4-11 is a well-characterized FLT3-dependent human cell line that contains internal tandem duplications (ITD) found in patients with acute myeloid leukemia and which express constitutively active Flt3 receptors (Yee et al. Blood 2002, 100(8), 2941-2949). This cell line was used to determine the ability of the compounds provided herein to inhibit Flt3 in intact cells. The RS4-11 cell line, which expresses the wild-type (WT) receptor, is also used as a control to verify the test compound's ability to inhibit the FLT3 receptor containing the ITD mutation. MV4-11 cell proliferation was measured after 72 hour incubation with the compounds provided herein, and RS4-11 after 48 hour incubation with the compounds provided herein, in both cases using a standard MTS protocol (Promega Cat #5430 "Cell Titer 96 Aqueous Non-radioactive Cell Proliferation Assay").

MV4-11 cells were plated at 10,000 cells per well in DMEM medium with 0.5% serum. RS4-11 cells were plated at 20,000 cells per well in RPMI with 0.5% serum. The compound plate was set up by aliquoting into column 1 of a 96 well 300 µL polypropylene plate, the negative control (DMSO), aliquoting into column 12 the positive control (an internal compound previously shown to have an $IC_{50}$ of 64 nM in the MV4-11 assay) and titrating the test compound in serial dilutions into columns 2-11. An aliquot from each well of the compound plate was transferred to the plated cells and then incubated at 37° C. in 5% $CO_2$ for 3 days for the MV4-11 cells and 2 days for the RS4-11 cells.

MTS tetrazolium compound (Owen's reagent) was thawed in a $H_2O$ bath. MTS tetrazolium (20 mL) was added to each well of optical plate and the cells were incubated at 37° C. in 5% $CO_2$ for 2 hours. The absorbance measured at 490 nm using Spectramax Plus 384 Absorbance Microplate Reader by Molecular Devices. Cell proliferation values are measured in terms of concentration of test compound that achieves 50% inhibition of cellular proliferation compared to control ($IC_{50}$) and are reported in Table 11 below.

Cell-Based Phosphorylation Study of the Compound of Formula I

The ability of the compound of Formula I to inhibit the kinase activity of FLT3 in the cellular environment was determined by measuring the extent of FLT3 phosphorylation in a leukemia cell line. MV4;11 cells, which harbor the FLT3 ITD mutation, were incubated with 5 different concentrations of the compound of Formula I (20 nM, 4 nM, 0.8 nM, 0.16 nM, and 0.032 nM). DMSO alone served as a negative control.

Inhibition of FLT3 autophosphorylation was determined by Western blot analysis of the FLT3 phosphorylation levels at the different concentrations of the compound of Formula I as compared to the phosphorylation level in the control. To control for sample-to-sample variation and gel loading differences, the level of phospho-FLT3 in each well was compared to the total amount of FLT3 present.

The results of FLT3-ITD (internal tandem duplication) autophosphorylation in MV4;11 cells was assessed using a FLT3 specific antibody. The compound of Formula I was shown to be a highly potent intracellular inhibitor of FLT3-ITD catalytic activity in the MV4;11 leukemia cell line. Semi-quantitative assessment of the potency of the compound of Formula I in the Western blot clearly showed significant inhibition of FLT3 phosphorylation with an $IC_{50}$ below 1 nM, as reported in Table 11. The compound of Formula I has an $IC_{50}$ of about 2 nM in FLT3/ITD-expressing cell lines and in primary FLT3/ITD AML patient blast samples. The compound of Formula I also displays a high degree of selectivity for FLT3 in an IL-3 rescue assay. The compound of Formula I also inhibits wild type FLT3 with an $IC_{50}$ of about 4 nM. The FLT3 binding affinity ($K_d$) of the compound of Formula I is about 1.6 nM.

TABLE 11

| Cell Line | Assay Type | $IC_{50}$ (nM) |
|---|---|---|
| MV4; 11 | FLT3 Autophosphorylation | 0.5-1.1 |
| MV4; 11 | Proliferation | 0.3-0356 |
| RS 4; 11 | Proliferation | 1,000 |

Example 2

Evaluation of the Compound of Formula I in the FLT3-Dependent Human Leukemia Cell Line MV4-11

The compound of Formula I was tested in xenograft mouse model in order to evaluate the in vivo activity at 1, 3, and 10 mg/kg against subcutaneous MV4-11 tumors in female athymic nude mice. Xenograft was initiated from MV4-11 FLT3-dependent human leukemia cells cultured in Iscove's Modified Dulbecco's medium supplemented with 10% heat-inactivated fetal bovine serum, 100 units/mL penicillin G, 100 μg/mL streptomycin sulfate, 0.25 μg/mL amphotericin B, 2 mM glutamine, 0.075% sodium bicarbonate, and 25 μg/mL gentamicin. Tumor cells were maintained in humidified atmosphere of 95% air and 5% $CO_2$ at 37° C. The cells were harvested during logarithmic phase growth and resuspended at a concentration of $5 \times 10^7$ cells/mL in 50% Matrigel matrix (BD Biosciences) and 50% PBS. MV4-11 cells ($1 \times 10^7$) were implanted subcutaneously into the right flank of each test mouse and the growth of tumors was monitored. Twelve days later, on Day 1 of the study, mice were placed in eight groups each consisting of ten mice with individual tumor sizes of 126 to 221 $mm^3$ and group mean tumor size of 174 $mm^3$, tumor volume calculated as a product of width×width×length in mm of an MV4-11 tumor. The compound of Formula I was formulated for dosing at 10 mL/kg and was administered by oral gavage (p.o.) once daily for 28 days. Each dose of drug was given in a volume of 0.2 mL per 20 g of body weight (10 mL/kg) and was adjusted for the body weight of the animal. Each animal was sacrificed when its tumor reached the predetermined endpoint size of 1,000 $mm^3$ or on the last day of the study (Day 59), whichever came first. FIG. 1 shows median tumor growth curves generated from the in vivo experiment which demonstrates that a representative compound provided herein produces dose-dependent antitumor activity. In this xenograft model, tumor regression was observed at 3 and 10 mg/kg (9 $mg/m^2$, p.o., QD), and tumor growth inhibition at 1 mg/kg (3 $mg/m^2$, p.o., QD).

In a follow-on study at the 10 mg/kg oral dose, tumor size was monitored for an additional 60 days after dosing was discontinued. By the end of the study eight complete responses and two partial responses were observed in the ten animals treated with the compound of Formula I. The compound of Formula I also had activity in a leukemia tumor model at doses as low as 1 mg/kg given orally once a day. A direct comparison of the compound of Formula I with the first generation FLT3 inhibitors CEP-701, MLN-518, PKC-412, sorafenib, and sunitinib revealed that the combination of potency, selectivity, and pharmacokinetic properties is unique to the compound of Formula I.

Example 3

Comparison of Human Exposure to Efficacious Exposure in Mice

Figure 2:
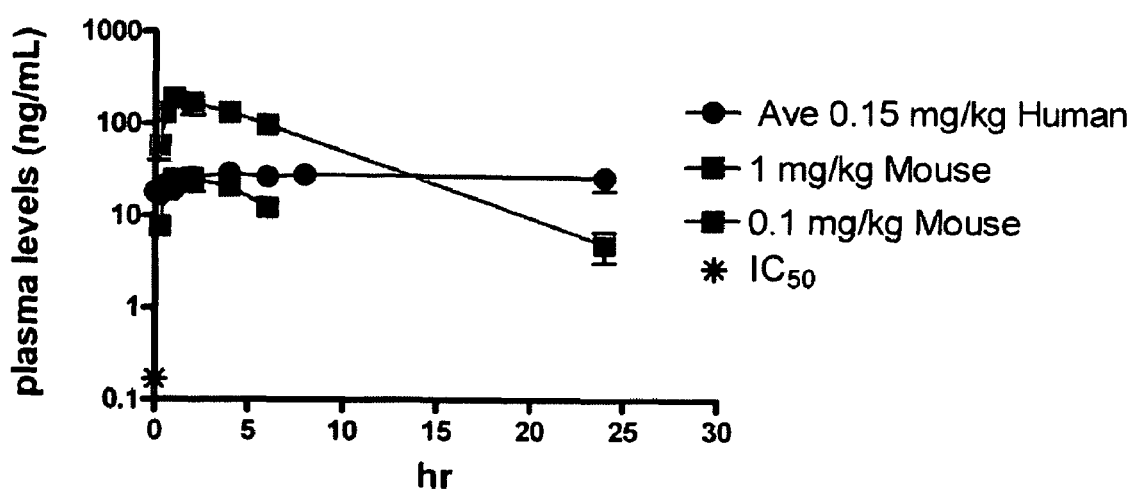
FIG. 2 depicts the plasma concentrations of N-(5-tert-butyl-isoxazol-3-yl)-N'-{4-[7-(2-morpholin-4-yl-ethoxy)imidazo[2,1-b][1,3]benzothiazol-2-yl]phenyl}urea over time in mice at a dose of 1 mg/kg or 0.1 mg/kg, and a human at a dose of about 0.15 mg/kg on average.

The xenograft experiment in Example 2 demonstrated that the compound of Formula I has efficacy in mice at 1 mg/kg p.o., QD. Exposure to the compound of Formula I was also found to be dose proportional in mice from 0.1-300 mg/kg PO (data not shown). Efficacious plasma levels in mice is shown to be about 800-fold over the MV4;11 $IC_{50}$ (exposure of approximately 3.2~μM*hr (AUC)) while human plasma levels ($C_p$) are about 200 fold and about 400 fold higher than the MV4;11 $IC_{50}$ at 12 and 18 mg, respectively (FIG. 2). Clinical exposure to the compound of Formula I measured by steady state plasma levels (SS $C_p$) predicts a human efficacious dose by about 60 mg. However, steady state exposure to the compound of Formula I is longer in humans (24 h) than mouse (6 h) (FIG. 2). Clinical exposure to the compound of Formula I as measured by Area Under the Concentration-Time Curve (AUC) predicts a human efficacious dose of about 20 mg.

When orally administered to mice at a dose of 10 mg/kg, the compound of Formula I achieved a peak plasma concentration ($C_{max}$) of 3.8 μM within two hours of dosing. When corrected for plasma protein biding, the concentration of the compound of Formula I in plasma remained above the cellular $IC_{50}$ for FLT3 inhibition 24 hours after dosing. Total exposure ($AUC_{0-24\ h}$) as well as $C_{max}$ increased proportionally with the administered dose from 0.1 to approximately 30 mg/kg. At higher doses, both $C_{max}$ and $AUC_{0-24\ h}$ continued to increase, approaching a plateau above 100 mg/kg.

TABLE 12

| Species | Dose | SS $C_p$ (ng/mL) | SS AUC0-24 (ng * h/mL) | ΔT(h) | Efficacy |
|---------|------|------------------|------------------------|-------|----------|
| Mouse | 1 mg/kg | 143 | 1793 | 6 | Yes |
| Human | 12 mg | 33 | 757 | 24 | Possible |
| Human | 18 mg | 60 | 1385 | 24 | Possible |

Example 4

Toxicity Studies of the Compound of Formula I in Rats and Dogs

Ninety-day toxicity profile of the compound of Formula I was evaluated in both rats and dogs. The compound of Formula I was formulated in 5% hydroxypropyl β-cyclodextrin (HPBCD). For rats, the compound was administered at a dose of 1, 3, or 10 mg/kg/day. No significant clinical signs were observed at low and middle doses. High dose produced elevations in liver function tests (LFTS), which is at about 2- to 3-folds, at an AUC of about 30 μM*hr or greater. Sustained neutropenia at high dose (very mild anemia) was observed. The terminal half-life of the compound of Formula I is 5.7 hours in rats.

For dogs, the compound was administered at a dose of 1, 5, or 15 mg/kg/day. No significant clinical signs were observed at low and middle doses. High dose produced elevations in liver function tests (LFTS), which is at about 3 to 6 folds, at an AUC of about 30 μM*hr or greater. Sustained neutropenia at high dose (very mild anemia) was observed. At the high dose, 10% weight gain suppression was observed. The terminal half-life of the compound of Formula I is 5.9 hours in dogs.

Example 5

Phase I Clinical Trial

This study was the first human clinical trial of the compound of Formula I in humans having relapsed or refractory acute myeloid leukemia. The study was open labeled and designed to determine the safety, tolerability, dose limiting toxicity (DLT), pharmacokinetics and pharmacodynamics of escalating doses. The compound of Formula I was orally administered starting at 12 mg QD for 14 days starting with a single-patient cohort. Since the first patient experienced an adverse event (not drug-related), the cohort was expanded to a three patient cohort and subsequently, the dose of the compound of Formula I was escalated in successive cohorts of at least three patients per dose level. Each new dose level began accrual only when all patients at the current dose level had been observed for a minimum of 14 days from the first day of dose administration and a minimum of three patients have completed at least one 14-day regimen of the compound of Formula I. When none of the first three patients at a dose level experienced first course dose limiting toxicity (DLT), then three new patients were entered the next higher dose level of up to 150% of the prior dose. When one of three patients experienced first course DLT, at least three more patients were started at that same dose level for a total of N=6. If two or more patients in the expanded cohort experiences first course DLT, no further patients will enroll at that dose and the next lower dose level will be declared the maximum tolerated dose (MTD). Primary endpoints for the study are safety, tolerability, dose limiting toxicity (DLT), and PK. Secondary endpoint is PD.

Three patients completed the first cohort. The first patient in Cohort 1 was 59 years old and weighed 81.2 kg when enrolled on Mar. 12, 2007. The patient was diagnosed with AML on Jun. 29, 2006 and treated subsequently with 4 chemotherapies. The disease relapsed on Mar. 6, 2007. FLT3 mutation was not detected in the patient upon genotyping. After enrollment, the patient successfully completed one fourteen-day dosing regimen at 12 mg per day of the compound of Formula I. No drug related adverse events or serious adverse events occurred. On Day 14, the patient was admitted to hospital for renal failure, which was determined to be not likely related to the study.

The second patient in Cohort 1 was 75 years old and weighed 78 kg when enrolled on May 14, 2007. The patient was diagnosed with AML on Aug. 16, 2005 and treated subsequently with three chemotherapies. The disease relapsed on Aug. 16, 2006. FLT3 mutation was not detected in the patient upon genotyping. After enrollment, the patient successfully completed two fourteen-day dosing regimens at 12 mg per day of the compound of Formula I. No drug related adverse events or serious adverse events occurred.

The third patient in Cohort 1 was a 27-year-old female and weighed 101 kg when she enrolled on Jul. 16, 2007. The patient was diagnosed with AML on Jul. 12, 2004 and treated subsequently with seven chemotherapies. The disease relapsed on May 31, 2007. FLT3 mutation was not detected in the patient upon genotyping. After enrollment, the patient successfully completed one fourteen-day dosing regimen at 12 mg per day of the compound of Formula I. No drug related adverse events or serious adverse events occurred.

Eight patients were enrolled in the second cohort. The first patient enrolled in Cohort 2 was an 82-year-old female and weighed 55 kg when she started the therapy on Aug. 7, 2007. The patient was diagnosed with AML on Jul. 31, 2007 and had no prior chemotherapeutic treatment. The patient voluntarily stopped treatment on Day 8, and no drug related adverse events or serious adverse events occurred.

The second patient in Cohort 2 was a 44-year-old female who weighed 55 kg when she started the therapy with the compound of Formula I Aug. 15, 2007. She was diagnosed with AML on Aug. 2, 2007 and was treated subsequently with four chemotherapies before the disease relapsed on Jul. 7, 2007. FLT3 mutation was not detected in the patient upon genotyping. After enrollment, the patient successfully completed two fourteen-day dosing regimens at 18 mg per day of the compound of Formula I. No drug related adverse events or serious adverse events occurred.

The third patient to enroll in Cohort 2 was a 78-year-old female who weighed 77 kg when she enrolled in the study on Aug. 15, 2007. She was diagnosed with AML on Aug. 3, 2007 and had no prior chemotherapeutic treatment. The FLT3 mutation at D835 was detected upon genotyping. The patient successfully completed two courses of the treatment with 18 mg of the compound of Formula I. The patient later died in October, which was deemed to be likely due to AML or comorbidities, but DLT assessment is still pending. This patient, however, exhibited major hematological improvement during treatment that could not be attributed to concomitant medications, procedures or blood transfusions. This patient's platelet count increased from 82 k/μL at the beginning of the first cycle of the treatment, to 158 k/μL by Day 19.

The fourth patient to enroll in Cohort 2 was a 72-year-old female who weighed 78 kg when she first received the therapy of the compound of Formula I on Aug. 22, 2007. She was diagnosed with AML on Aug. 2, 2007 and received one chemotherapy after which the disease was deemed refractory. FLT3 mutation was not detected in the patient upon genotyping. The patient received 7 days of the compound of Formula I at which point she experienced multiple grade 3 adverse events which included acute congestive heart failure. The patient later died. The congestive heart failure was found to have been a pre-existing but the SAE was deemed to be possibly drug related and was therefore reported as a DLT. This patient, however, exhibited minor hematological improvement following treatment that could not be attributed to concomitant medications, procedures or blood transfusions. The patient's absolute neutrophil count (ANC) increased by $1.3 \times 10^9/L$ eight days after the first dose of the compound of Formula I, and the count continued to increase by up to $2.6 \times 10^9/L$ seventeen days after the first dose.

Since the fourth patient to enroll in Cohort 2 experienced a DLT, the cohort was expanded to include at least three more patients. The fifth patient to enroll in Cohort 2 was a 72-year-old male who weighed 86 kg when he started a therapy of the compound of Formula I on Sep. 6, 2007. He was diagnosed with AML in Dec. 28, 2006 and received two chemotherapies before the disease relapsed on Aug. 6, 2007. FLT3 mutation was not detected in the patient upon genotyping. The patient successfully completed three courses of the therapy and a fourth course is currently on-going. No drug related adverse events or serious adverse events have occurred. This patient exhibited major hematological improvement following treatment that could not be attributed to concomitant medications, procedures or blood transfusions. This patient exhibited a decrease in bone marrow blast, from 63% at Day 0 of the first cycle of the treatment with the compound of Formula I, down to 15% at Day 15 of the first cycle. The patient also showed a decrease in peripheral blast, from 9% at Day 0 of the first cycle of the therapy, down to 0% at Day 15 of the first cycle.

The sixth patient to enroll in Cohort 2 was a 72-year-old male who weighed 72 kg when he started a therapy with the compound of Formula I on Sep. 24, 2007. He was diagnosed with AML on Aug. 2, 2002 and received eight prior chemotherapies. FLT3 mutation was not detected in the patient upon genotyping. The patient successfully completed one course of the therapy and voluntarily discontinued treatment during the second course. No drug related adverse events or serious adverse events occurred.

The seventh patient in Cohort 2 was a 36-year-old male who weighed 89 kg when he started a therapy with the compound of Formula I on Sep. 24, 2007. He was diagnosed with AML on Mar. 23, 2006 and received seven prior chemotherapies, before the disease relapsed on Sep. 10, 2007. The patient only received 10 days of the therapy. No drug related adverse events or serious adverse events occurred.

The eighth patient in Cohort 2 was a 51-year-old male who weighed 67 kg when he started a therapy with the compound of Formula I on Sep. 25, 2007. The patient was diagnosed with AML on May 16, 2007, and received four prior chemotherapies, before the disease relapsed. FLT3 mutation was not detected in the patient upon genotyping. The patient successfully completed three courses of the therapy. No drug related adverse events or serious adverse events occurred.

As no additional DLTs were observed for Cohort 2, patients were enrolled in the third cohort at the dose of 27 mg. The first patient in Cohort 3 was a 49-year-old male who weighed 84 kg when he started a therapy with the compound of Formula I on Oct. 15, 2007. The patient was diagnosed with AML on Jan. 31, 2007 and received two prior chemotherapies before the disease relapsed on Sep. 28, 2007. FLT3 mutation was not detected in the patient upon genotyping. The patient successfully completed three courses of the therapy and voluntarily discontinued treatment during the second course. No drug related adverse events or serious adverse events occurred.

The second patient enrolled in Cohort 3 was an 86-year-old female who weighed 62 kg when she started a therapy with the compound of Formula I on Oct. 17, 2007. The patient was diagnosed with myelodysplastic syndrome (MDS) and was treated with prior chemotherapies before being diagnosed with AML on Oct. 11, 2007. The patient voluntarily discontinued the treatment on Day 7. No drug related adverse events or serious adverse events occurred.

The third patient enrolled in Cohort 3 was a 64-year-old female who weighed 82 kg when she started a therapy with the compound of Formula I on Oct. 16, 2007. The patient was diagnosed with AML in April of 2007 and received two prior chemotherapies until the disease relapsed on Oct. 8, 2007. The patient received only 8 days of treatment when he was withdrawn from the study by the investigator due to disease progression. No drug related adverse events or serious adverse events occurred.

The fourth patient enrolled in Cohort 3 was a 68-year-old male who weighed 66 kg when he started a therapy with the compound of Formula I on Oct. 25, 2007. The patient was diagnosed with AML on Sep. 28, 2006 and received two prior chemotherapies. The patient successfully completed one course of the therapy and started on a second course. No drug related adverse events or serious adverse events occurred.

The fifth patient enrolled in Cohort 3 was a 57-year-old female who started a therapy with the compound of Formula I on Nov. 28, 2007. She successfully completed one course of the therapy and started on a second course.

The sixth patient enrolled in Cohort 3 was a 78-year-old male who started a therapy with the compound of Formula I on Nov. 16, 2007. He successfully completed two courses of the therapy. No drug related adverse events or serious adverse events occurred.

As MTD (the maximum tolerated dose, or the highest dose level in which less than two of the six patients developed first cycle DLT) was not reached for Cohort 3, patients are currently being enrolled for Cohort 4. Among the patients in Cohorts 1 and 2, there most common Grade 1 (mild) drug-related adverse events included two instances of nausea/vomiting, two instances of abdominal distension/constipation, one instance of cough, one instance of decreased appetite and one instance of disgeusia. Two deaths occurred, one due to an unrelated fungal infection, and a second due to congestive heart failure that was deemed to be possibly drug related, in a patient who was later found to have had a pre-existing case of CHF. The patient with CHF was the only patient of the two cohorts, who experienced a grade 3 drug-related adverse event. However, no hematological toxicity was observed in either cohorts.

Figure 3:
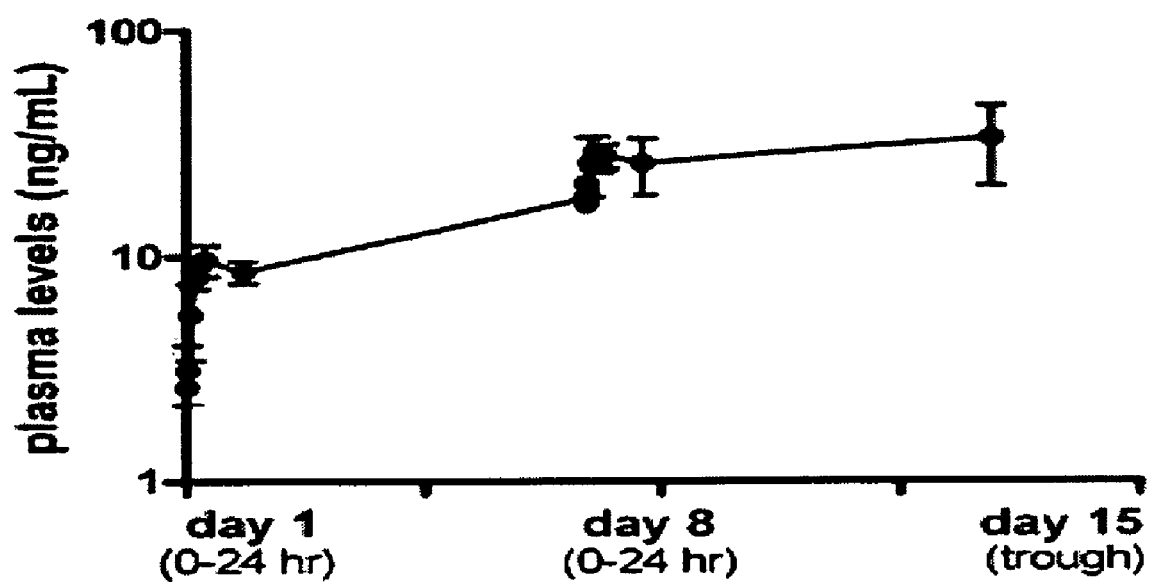
FIG. 3 depicts the plasma concentrations of N-(5-tert-butyl-isoxazol-3-yl)-N'-{4-[7-(2-morpholin-4-yl-ethoxy)imidazo[2,1-b][1,3]benzothiazol-2-yl]phenyl}urea over time in human under a multiple dosing regime: the first dose was at the beginning of day 1 and the second dose was at day 8.

Human oral PK data from the clinical trial patients was modeled in WinNonlin using noncompartmental analysis and a linear-trapezoidal fit. Pharmacokinetic data for Cohort 1 is summarized in Table 13. The result is shown in FIGS. 2 and 3. The weight range for these patients is 77.9 to 101.25 kg. The average plasma concentrations at the 12 mg dose are 11.2 ng/mL at day 1, 37.9 ng/mL at day 8, and 42.9 ng/mL (0.06 mM) at steady state by day 15. Steady state was achieved at 1-2 weeks with minor peaks and troughs with an apparent terminal half-life of about 2.8 days. At the initial 12 mg dose, human plasma levels are approximately 0.06 µM at steady state. Inter-patient variability of steady state plasma concentrations within the three-patient cohort is low. The compound of Formula I appears to have good bioavailability in humans and the plasma exposure variability among first three patients is low.

Figure 4A:
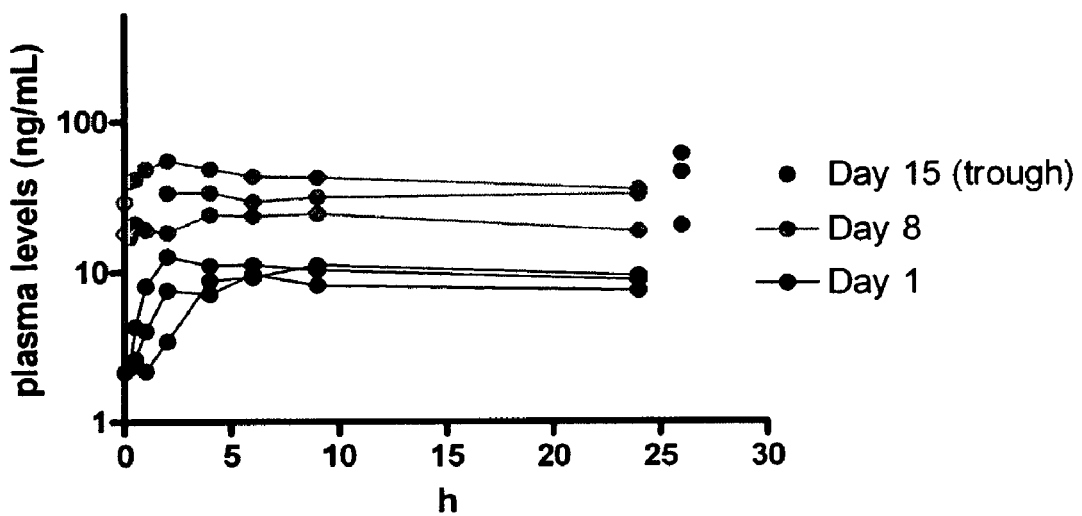
FIG. 4 depict the plasma concentrations of N-(5-tert-butyl-isoxazol-3-yl)-N'-{4-[7-(2-morpholin-4-yl-ethoxy)imidazo[2,1-b][1,3]benzothiazol-2-yl]phenyl}urea over time for each patient in the 12 mg cohort and 18 mg cohort.
Figure 4B:
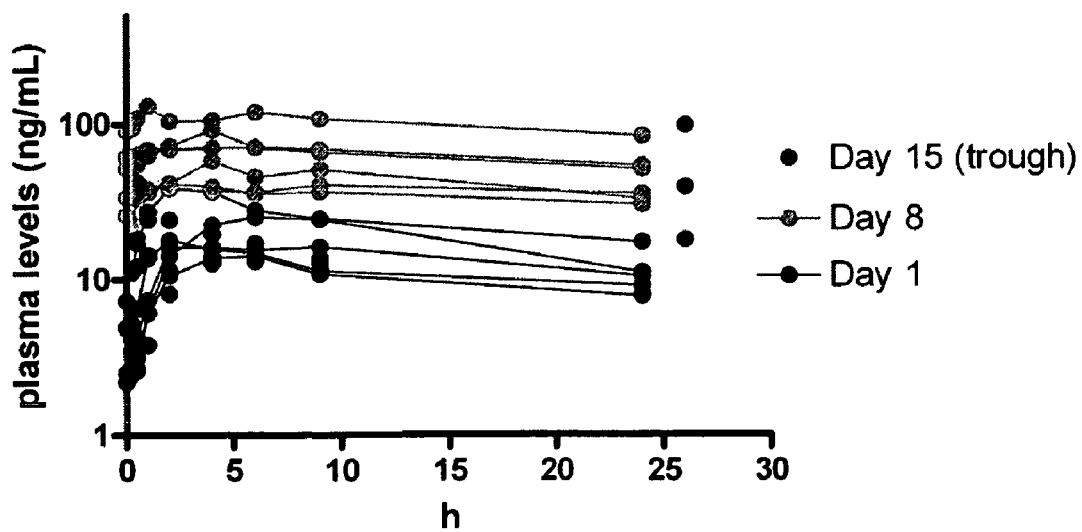
Figure 5A:
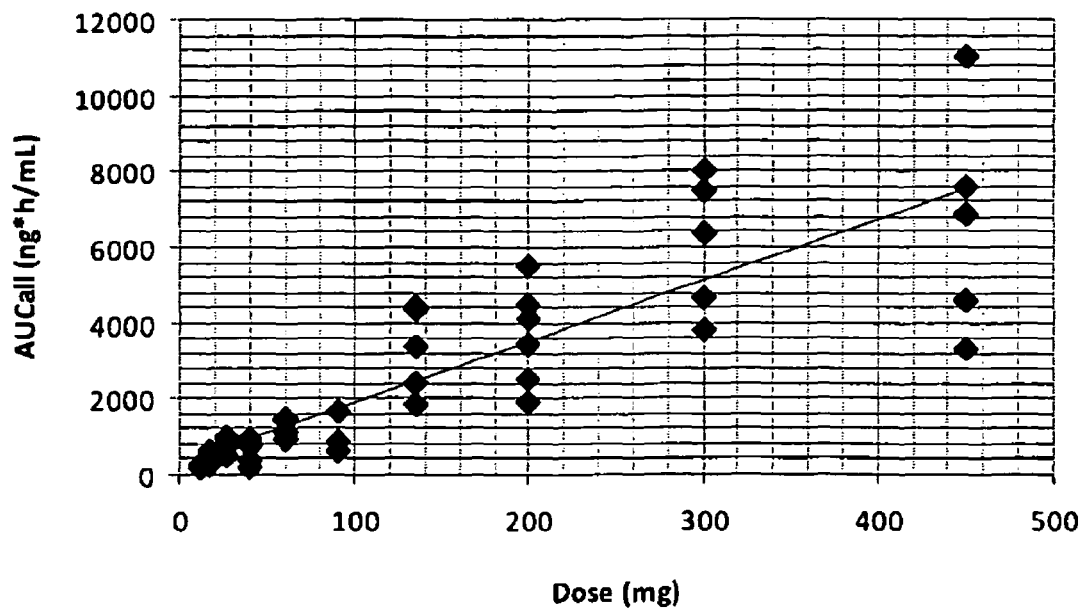
FIG. 5 depict the dose response of the exposure (AUC) in humans to N-(5-tert-butyl-isoxazol-3-yl)-N'-{4-[7-(2-morpholin-4-yl-ethoxy)imidazo[2,1-b][1,3]benzothiazol-2-yl]phenyl}urea at day 1 (FIG. 5A) and day 8 (FIG. 5B).
Figure 5B:
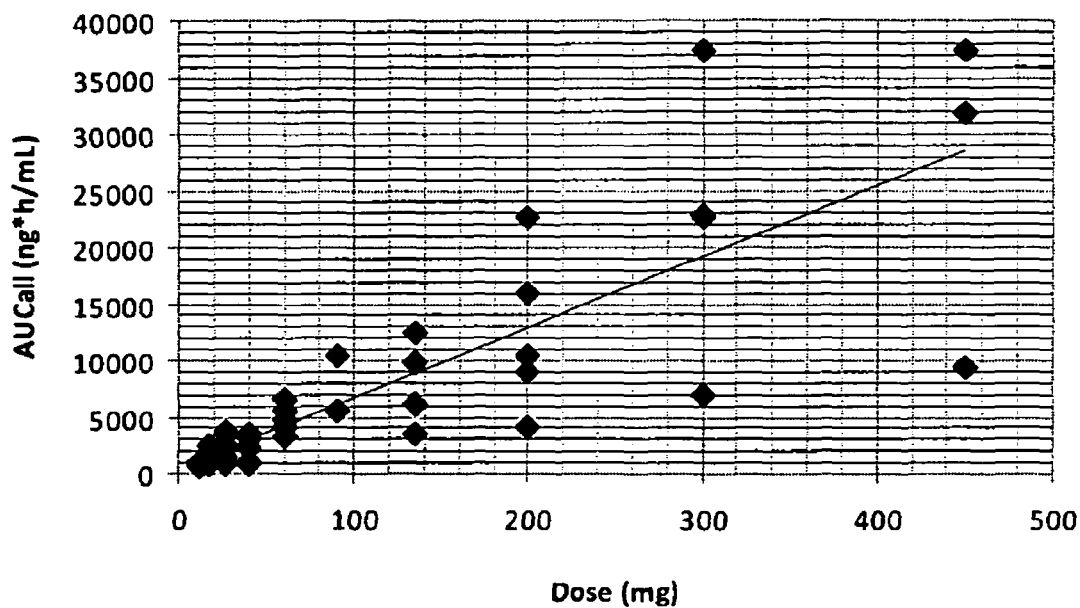

Pharmacokinetic data for Cohort 2 is summarized in Table 14. The result is shown in FIG. 4. The weight range for these patients is 54.9 kg to 88.5 kg. The average plasma concentrations at the 18 mg dose are 21.1 ng/mL at day 1 (N=8), 72.5 ng/mL at day 8 (N=6) and 51.8 ng/mL at day 15 (N=3). The two cohorts taken together, show good human bioavailability and shows low intra-patient variability of plasma exposure within each cohort. The two cohort data shows a steady state that was achieved at 1-2 weeks with minor peaks and troughs with an apparent terminal half-life of about 1-2.8 days. Biological activity of the compound of Formula I was observed in three different patients in cohort 2 in the way of hematological improvement, and in one patient, a partial response of greater than 50% reduction in bone marrow blasts was observed.

Pharmacokinetic data for two patients in Cohort 3 is summarized in Table 15. One patient in Cohort 3 (27 mg/day) was dosed with the compound of Formula I continuously for 42 days with acceptable tolerability and no DLT, before he elected to have no further treatment.

A clinical study of the compound of Formula I included a standard 3+3 dose escalation design with 50% dose increments. For example, the compound of Formula I was administered once daily as an oral solution for 14 days, followed by a 14-day rest period (1 cycle) with a starting dose of 12 mg. Concurrently, patients were being dosed on a continuous dosing regimen starting at 200 mg/day for 28 days. Patients showing clinical benefit may continue to receive further cycles of therapy. Fifty two patients were dosed with the compound of Formula I up to 450 mg/day (10 dose cohorts). Median age was 60 years, ranging from 23 to 86 years, median number of prior therapies was 3, ranging from 0 to 8, and 2 patients were with prior allogeneic hematopoietic stem cell transplant (HSCT). Two elderly patients (age≧78 yrs) unfit for induction chemotherapy were previously untreated. Fifteen patients had FLT3 mutations (12 ITD and 3 TKD), 25 patients were WT, and 12 patients were undetermined. Patients are also evaluated for PK, pFLT3, pSTAT5, FLT3 genotyping, and ex vivo plasma inhibitory activity. The compound of Formula I was well tolerated and MTD has not yet been observed with either schedule. One patient had a possibly drug-related DLT in the 18 mg cohort (grade 3 CHF, although the patient had a pre-existing heart condition) leading to cohort expansion, but no other cases of drug-related CHF or other DLT have been seen to date. Other possibly drug-related AEs (most frequently gastrointestinal events) were mild (grade≦2). Response data based on investigator's assessment were available on the first 45 pts. To date, responses were observed in 11 patients (24%). Four patients achieved a complete response (CR)-2 with incomplete platelet recovery (CRp) and 2 with incomplete platelet and neutrophil recovery (CRi), one of these patients also had complete resolution of leukemia cutis. In addition, 7 patients had partial responses (PR, defined as a decrease of ≧50% blasts to levels of 5%-25% in the bone marrow). Most responses (8/11, 73%) occurred after cycle 1 and one was observed after cycle 3. Median duration of response is 18 weeks (range, 4 to 26+ weeks). Three responders were FLT3 mutants (2 ITD and 1TKD), five were WT, three were undetermined. Six of the 9 non-responding patients with ITD mutations had initial rapid clearing of peripheral blasts with intermittent dosing of the compound of Formula I, but subsequently progressed or had disease-related mortality. All these patients had aggressive disease and received a median of 6 prior treatment regimens, ranging 3 to 8). Plasma exposure to the compound of Formula I was sustained between dose intervals and continued to increase in a dose proportional manner from 12 mg to 300 mg daily, with steady-state plasma concentrations achieving greater than 1,500 nM at 300 mg. FLT3 phosphorylation was strongly suppressed when plasma obtained from study patients was tested ex vivo in FLT3-ITD and WT cell lines at 12 mg and 60 mg doses, respectively.

Certain patients in the 60 mg cohort and 200 mg cohort who started with the 14-day dosing followed by 14 day rest regimen switched to a continuous dosing regimen.

The protocol describing the 14-day dosing followed by 14 day rest was also amended to permit a continuous dosing regimen starting at 200 mg/day for 28 days (1 cycle). Patients with clinical benefit would continue to receive further cycles.

TABLE 13

| Group | Patient ID | Dose mg | Dose mg/kg | $C_{max}$ ng/mL | $T_{max}$ h | AUC (0-24) (ng/mL) * h | $C_{max}$ μM | $T_{max}$ h | AUC (0-24) μM * h |
|---|---|---|---|---|---|---|---|---|---|
| Day 1-2 | 1 | 12 | 0.14 | 11.2 | 8 | 205 | 0.02 | 8 | 0.37 |
| Day 1-2 | 2 | 12 | 0.16 | 9.71 | 6 | 184 | 0.02 | 6 | 0.33 |
| Day 1-2 | 3 | 12 | | 12.7 | 2 | 238 | 0.02 | 2 | 0.43 |
| Day 8-9 | 1 | 12 | 0.14 | 33.9 | 4 | 744 | 0.06 | 4 | 1.33 |
| Day 8-9 | 2 | 12 | 0.16 | 24.5 | 9 | 525 | 0.04 | 9 | 0.94 |
| Day 8-9 | 3 | 12 | | 55.2 | 2 | 1003 | 0.10 | 2 | 1.79 |
| Day 15 | 1 | 12 | 0.14 | 46.5 | 2 | — | 0.08 | 2 | — |
| Day 15 | 2 | 12 | 0.16 | 20.5 | 2 | — | 0.04 | 2 | — |
| Day 15 | 3 | 12 | | 61.6 | 2 | — | 0.11 | 2 | — |

TABLE 14

| Group | Patient ID | Dose mg | Dose mg/kg | $C_{max}$ ng/mL | $T_{max}$ h | AUC (0-24) (ng/mL) * h | $C_{max}$ μM | $T_{max}$ h | AUC (0-24) μM * h |
|---|---|---|---|---|---|---|---|---|---|
| Day 1-2 | 1 | 18 | — | 14.5 | 1 | 269 | 0.03 | 1 | 0.48 |
| Day 1-2 | 2 | 18 | — | 14.2 | 6 | 241 | 0.03 | 6 | 0.43 |
| Day 1-2 | 3 | 18 | — | 17.9 | 2 | 279 | 0.03 | 2 | 0.50 |
| Day 1-2 | 4 | 18 | — | 16.3 | 9 | 329 | 0.03 | 9 | 0.59 |
| Day 1-2 | 5 | 18 | — | 38.9 | 2 | 583 | 0.07 | 2 | 1.04 |
| Day 1-2 | 6 | 18 | — | 24.4 | 2 | 404 | 0.04 | 2 | 0.72 |
| Day 1-2 | 7 | 18 | — | 17.1 | 9 | 314 | 0.03 | 9 | 0.56 |
| Day 1-2 | 8 | 18 | — | 25.2 | 6 | 437 | 0.04 | 6 | 0.78 |
| Day 8-9 | 2 | 18 | — | — | — | — | — | — | — |
| Day 8-9 | 3 | 18 | — | 40.4 | 9 | 906 | 0.07 | 9 | 1.62 |
| Day 8-9 | 4 | 18 | — | 58.2 | 4 | 1058 | 0.10 | 4 | 1.89 |
| Day 8-9 | 5 | 18 | — | 131.8 | 1 | 2445 | 0.24 | 1 | 4.36 |
| Day 8-9 | 6 | 18 | — | 71.2 | 6 | 1496 | 0.13 | 6 | 2.67 |
| Day 8-9 | 7 | 18 | — | 41.2 | 2 | 823 | 0.07 | 2 | 1.47 |
| Day 8-9 | 8 | 18 | — | 92.3 | 4 | 1581 | 0.16 | 4 | 2.82 |
| Day 15 | 1 | 18 | — | (2.6) | 2 | — | (0.00) | 2 | — |
| Day 15 | 2 | 18 | — | (2.2) | 2 | — | (0.00) | 2 | — |
| Day 15 | 3 | 18 | — | 18.0 | 2 | — | 0.03 | 2 | — |
| Day 15 | 4 | 18 | — | 39.5 | 2 | — | 0.07 | 2 | — |
| Day 15 | 5 | 18 | — | 98.0 | 2 | — | 0.17 | 2 | — |

TABLE 15

| Group | Patient ID | Dose mg | Dose mg/kg | $C_{max}$ ng/mL | $T_{max}$ h | AUC (0-24) (ng/mL) * h | $C_{max}$ μM | $T_{max}$ h | AUC (0-24) μM * h |
|---|---|---|---|---|---|---|---|---|---|
| Day 1-2 | 1 | 27 | — | 53.8 | 2 | 953 | 0.10 | 2 | 1.70 |
| Day 1-2 | 2 | 27 | — | 37.3 | 6 | 757 | 0.07 | 6 | 1.35 |
| Day 8-9 | 1 | 27 | — | 197.0 | 2 | 1386 | 0.35 | 2 | 2.47 |
| Day 8-9 | 2 | 27 | — | 222.0 | 1 | 3419 | 0.40 | 1 | 6.10 |

Example 6

Preparation of the Compound of Formula I Capsules 75 mg

Capsules 75 mg is comprised of 75 mg of a dihydrochloride salt of the compound of Formula I, suspended in a waxy matrix of lauroyl polyoxylglycerides (GELUCIRE® 44/14, Gattefosse). To produce approximately 4,000 Capsules 75 mg, a mixture of a dihydrochloride salt of the compound of Formula I (300 g) and GELUCIRE® 44/14 (1,900 g) in a suitably sized jacketed vessel was stirred at approximately 70° C. until molten. The molten mixture was slowly charged into the vortex of a container and mixed until a homogeneous suspension was obtained. The suspension was maintained at a blend temperature of 70° C. and deaerated under vacuum. With gentle mixing to avoid incorporation of air, the suspension was allowed to cool to a temperature of 50° C. The suspension was then charged into a heated hopper attached to a CAPSUGEL® CSF1200 or similar encapsulation machine. Each capsule was filled with the suspension to an average weight of 550 mg. The finished capsules were allowed to cool prior to packaging into appropriate containers.

Example 7

Preparation of the Compound of Formula I Powder in Bottle 350 mg

Powder in Bottle 350 mg is comprised of 350 mg of a dihydrochloride salt of the compound of Formula I and no additional excipients. To produce 2,000 bottles, a dihydrochloride salt of the compound of Formula I (350 mg) was weighed using a calibrated balance into a 100 mL bottle. Each bottle was sealed with a rubber stopper and a flip off seal.

Powder in Bottle 350 was reconstituted prior to use with a 5% solution of hydroxypropyl-β-cyclodextrin to a concentration of 5 mg/mL of a dihydrochloride salt of the compound of Formula I. The reconstituted compound of Formula I was dosed as an oral solution.

Example 8

Preparation of the Compound of Formula I Lyophilized Powder in Bottle 75 mg

Lyophilized Powder in Bottle 75 mg is comprised of 75 mg of a dihydrochloride salt of the compound of Formula I and 75 mg of hydroxypropyl-β-cyclodexin. To produce 4,000 bottles, a solution of hydroxypropyl-β-cyclodexin (6 L) was prepared by dissolving hydroxypropyl-β-cyclodexin (3 kg) in a suitable container. With continued agitation, the dihydrochloride salt of the compound of Formula I (300 g) was added to the solution, and mixed until dissolved, if necessary, with heat. The solution was filtered before filling. Each 30 mL bottle was filled with 15 mL of the solution. After the filling, the solution in each bottle was flash frozen and lyophilized. The bottle was then sealed tightly.

Prior to dosing, Lyophilized Powder in Bottle 75 was reconstituted by adding 15 mL of water to the bottle and swirling the bottle gently for one minute until powder was dissolved. The reconstituted compound of Formula I was dosed as an oral solution.

Example 9

Additional Formulations

Additional formulations that were prepared are summarized in Table 16, along with methods of their preparation. Certain formulations in Table 16 were studied in vivo.

TABLE 16

| Formulation | Preparation |
| --- | --- |
| 3 mg/mL of the compound of Formula I in a 22% HPBCD solution | a. Prepare a 22% HPBCD solution. b. Dissolve 3 mg of the compound of Formula I in 1 mL of the HPBCD solution |
| 1, 3, 10 mg/mL of the compound of Formula I in a 22% HPBCD Solution | a. Prepare a 22% HPBCD solution. b. Dissolve 1, 3, or 10 mg of the compound of Formula I in 1 mL of the HPBCD solution |
| The compound of Formula I in PEG 400 and Water (3:1) | a. Add PEG400 to the compound of Formula I (75% of total volume required for 1 mg/mL) and vortex or sonicate until in solution. b. Slowly add water while swirling (25% of total volume required for 1 mg/mL) and vortex of sonicate to mix well |
| 3 mg/mL of the compound of Formula I in a 5% HPBCD Solution | a. Prepare a 5% HPBCD solution. b. Dissolve 30 mg of the compound of Formula I in 10 mL of the HPBCD solution |
| The compound of Formula I (75 mg) Mannitol (282 mg) EXPLOTAB ® (22.8 mg) | a. Weigh out individual ingredients b. Blend and fill capsules. |
| The compound of Formula I (25 mg) Mannitol (332 mg) EXPLOTAB ® (22.8 mg) | a. Weigh out individual ingredients b. Blend and fill capsules. |
| The compound of Formula I (75 mg) Mannitol (206 mg) EXPLOTAB ® (22.8 mg) Citric Acid (76 mg) | a. Weigh out individual ingredients b. Blend and fill capsules. |
| The compound of Formula I (25 mg) Mannitol (309 mg) EXPLOTAB ® (22.8 mg) Citric Acid (25 mg) | a. Weigh out individual ingredients b. Blend and fill capsules. |
| 5 mg/mL of the compound of Formula I in 5% HPBCD | a. Prepare a 5% HPBCD solution. b. Dissolve 5 mg of the compound of Formula I in 1 mL of the HPBCD solution. |

TABLE 16-continued

| Formulation | Preparation |
|---|---|
| Hot Melt Granulation<br>PEG6000 (31%)<br>Mannitol (43.3%)<br>EXPLOTAB ® (12%)<br>The compound of Formula I (50 mg) | 1. Melt PEG, mannitol, and the compound of Formula I.<br>2. Dry, screen, and then blend with remaining mannitol and EXPLOTAB ®. |
| Hot Melt Granulation<br>PEG6000 (18.8%)<br>Mannitol (61.2%)<br>EXPLOTAB ® (12%)<br>The compound of Formula I (30 mg) | 1. Melt PEG, mannitol, and the compound of Formula I.<br>2. Dry, screen, and then blend with remaining mannitol and EXPLOTAB ®. |
| Wet Granulation<br>The compound of Formula I (75 mg)<br>Mannitol (226 mg)<br>PVP (14 mg)<br>EXPLOTAB ® (35 mg) | 1. Granulate PVP solution, EXPLOTAB ®, mannitol, and the compound of Formula I.<br>2. Dry, screen, and blend with remaining EXPLOTAB ® and mannitol. |
| Wet Granulation<br>The compound of Formula I (25 mg)<br>Mannitol (276 mg)<br>PVP (14 mg)<br>EXPLOTAB ® (35 mg) | 1. Granulate PVP solution, EXPLOTAB ®, mannitol, and the compound of Formula I.<br>2. Dry, screen, and blend with remaining EXPLOTAB ® and mannitol. |
| Micronized the compound of Formula I<br>The compound of Formula I (75 mg)<br>Mannitol (282 mg)<br>EXPLOTAB ® (22.8 mg) | 1. Prepare micronized compound of Formula I using Jet-mill.<br>2. Weigh out individual ingredients, blend, and fill capsule. |
| Micronized the compound of Formula I<br>The compound of Formula I (25 mg)<br>Mannitol (332 mg)<br>EXPLOTAB ® (22.8 mg) | 1. Prepare micronized compound of Formula I using Jet-mill 2. Weigh out individual ingredients, blend, and fill capsule. |
| Liquid Fill<br>The compound of Formula I (50 mg)<br>GELUCIRE ® 44/14 (470 mg) | 1. Heat GELUCIRE ® until liquid.<br>2. Disperse the compound of Formula I into GELUCIRE ®.<br>3. While warm, dispense the suspension into capsules. |
| 3 mg/mL of the compound of Formula I in a 5% HPBCD Solution | 1. Prepare a 5% HPBCD solution.<br>2. Dissolve 30 mg of the compound of Formula I in 10 mL of the solution |
| 18 mg/mL of the compound of Formula I in GELUCIRE ® | 1. Heat GELUCIRE ® until liquid.<br>2. Disperse the compound of Formula I into GELUCIRE ®.<br>3. While warm, dispense the suspension into capsules. |
| 75% GELUCIRE ® 44/14<br>25% PEG6000 | 1. Heat GELUCIRE ® and PEG6000 separately until liquid.<br>2. Combine the two and then dispense the compound of Formula I into mixture.<br>3. While warm, dispense the suspension into capsules. |
| The compound of Formula I (70 mg)<br>Mannitol (275.5 mg)<br>EXPLOTAB ® (22.8 mg)<br>PLURONIC ® F68 (11.4 mg) | 1. Blend the compound of Formula I with powder components by geometric dilution.<br>2. Dispense blended powder into capsules |
| The compound of Formula I (164 mg/mL) in GELUCIRE ®:<br>The compound of Formula I (100 mg)<br>GELUCIRE ® 44/14 (0.7 mL) | 1. Heat GELUCIRE ® until liquid.<br>2. Disperse the compound of Formula I into GELUCIRE ®.<br>3. While warm, dispense the suspension into capsules |
| GELUCIRE ® Hot Melt<br>The compound of Formula I (60 mg)<br>GELUCIRE ® 44/14 (37.5 mg)<br>PEG 6000 (112.5 mg)<br>Silicone Dioxide (10 mg)<br>Mannitol (117.5 mg)<br>EXPLOTAB ® (37.5 mg) | 1. Mix GELUCIRE ® with liquid the compound of Formula I to form a suspension.<br>2. Melt PEG 6000 and mannitol together and then mix with the suspension.<br>3. Dry, screen, and blend with remaining mannitol and EXPLOTAB ®. |
| The compound of Formula I (150 mg/mL) in GELUCIRE ®:<br>The compound of Formula I (63 mg)<br>GELUCIRE ® 44/14 (0.5 mL) | 1. Heat GELUCIRE ® until liquid.<br>2. Disperse the compound of Formula I into GELUCIRE ®.<br>3. While warm, dispense the suspension into capsules |
| The compound of Formula I (125 mg/mL) in GELUCIRE ®:<br>The compound of Formula I (55 mg)<br>GELUCIRE ® 44/14 (0.5 mL) | 1. Heat GELUCIRE ® until liquid.<br>2. Disperse the compound of Formula I into GELUCIRE ®.<br>3. While warm, dispense the suspension into capsules |
| The compound of Formula I (70 mg)<br>HPBCD (140 mg)<br>Mannitol (119 mg)<br>EXPLOTAB ® (21 mg) | 1. Mix the compound of Formula I and HPBCD.<br>2. Lyophilize |
| Lyophilized material (110 mg) | 1. Prepare a 5% HPBCD solution. |

TABLE 16-continued

| Formulation | Preparation |
|---|---|
| The compound of Formula I (10 mg) HPBCD (100 mg) Material reconstituted to 5 mg/ml with water | 2. Dissolve 5 mg of the compound of Formula I in 1 mL of 5% HPBCD solution. 3. Freeze the solution and lyophilize over night. |
| Lyophilized material (60 mg) The compound of Formula I (10 mg) HPBCD (50 mg) Material reconstituted to 5 mg/ml with water | 1. Prepare a 5% HPBCD solution. 2. Dissolve 10 mg of the compound of Formula I in 1 mL of 5% HPBCD solution. 3. Freeze the solution and lyophilize over night. |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating a proliferative disease in a mammal, which comprises administering to the mammal having or suspected to have the proliferative disease, a therapeutically effective amount of the compound of Formula I:

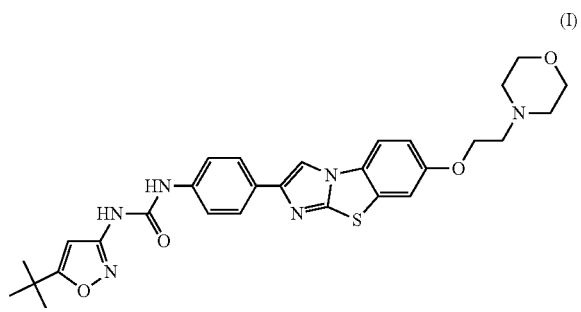

(I)

or a pharmaceutically acceptable salt or solvate thereof, wherein the therapeutically effective amount is at least 12 mg per day; and wherein the proliferative disease is selected from the group consisting of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

2. The method of claim 1, wherein the therapeutically effective amount is from about 40 to 450 mg per day.

3. The method of claim 1, wherein the compound is administered intermittently.

4. The method of claim 1, wherein the compound is administered continuously.

5. The method of claim 4, wherein the therapeutically effective amount is from about 27 to about 1000 mg per day.

6. A method of treating a proliferative disease in a mammal, which comprises administering to the mammal having or suspected to have the proliferative disease, a therapeutically effective amount of the compound of Formula I:

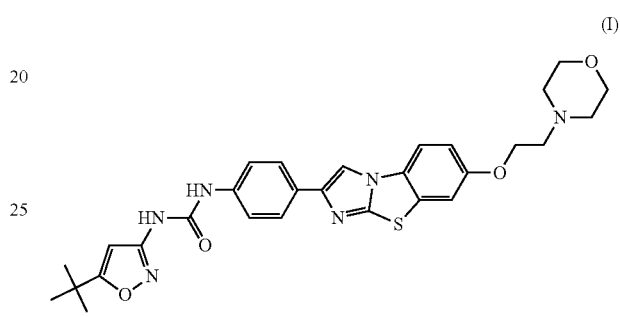

(I)

or a pharmaceutically acceptable salt or solvate thereof, wherein the therapeutically effective amount is from about 0.1 to about 10 mg/kg/day; and wherein the proliferative disease is selected from the group consisting of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

7. A method of treating a proliferative disease in a mammal, which comprises administering to the mammal having or suspected to have the proliferative disease a therapeutically effective amount of the compound of Formula I:

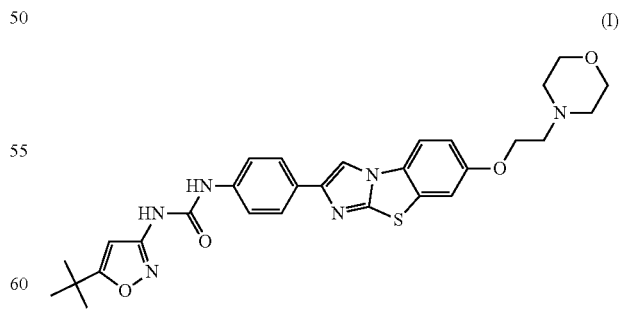

(I)

or a pharmaceutically acceptable salt or solvate thereof, wherein the amount administered is sufficient to provide a plasma concentration at steady state, of about 0.01 to about 10 μM of the compound; and wherein the proliferative disease is selected from the group consisting of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

8. A method of treating a proliferative disease in a mammal, which comprises administering to the mammal having or suspected to have the proliferative disease a therapeutically effective amount of the compound of Formula I:

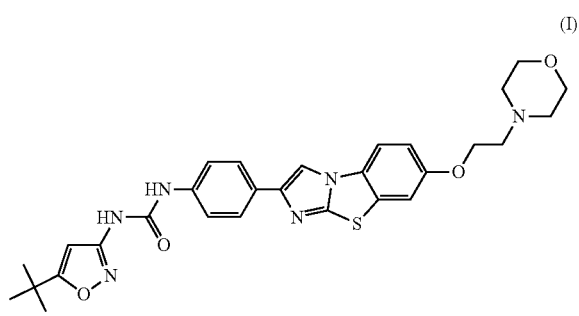

(I)

or a pharmaceutically acceptable salt or solvate thereof, wherein the amount administered is sufficient to provide a peak plasma concentration of about 0.01 to about 10 μM of the compound and wherein the proliferative disease is selected from the group consisting of a leukemia, myeloma, myeloproliferative disease, myelodysplastic syndrome, idiopathic hypereosinophilic syndrome (HES), bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, and hematologic malignancy.

9. The method of claim 1, wherein the compound is a dihydrochloride salt.

10. The method of claim 1, wherein the proliferative disease is a leukemia.

11. The method of claim 10, wherein the leukemia is an acute leukemia.

12. The method of claim 11, wherein the leukemia is acute myeloblastic leukemia.

13. The method of claim 11, wherein the leukemia is promyelocytic leukemia.

14. The method of claim 11, wherein the leukemia is acute lymphoblastic leukemia.

15. The method of claim 1, wherein the proliferative disease is acute myelogenous leukemia (AML), chronic myelogenous leukemias (CML), myelodysplastic leukemia, chronic eosinophilic leukemia (CEL), chronic myelomonocytic leukemia (CMML), mast cell leukemia, or systemic mastocytosis.

16. The method of claim 10, wherein the leukemia is relapsed or refractory.

17. The method of claim 10, wherein the leukemia is a drug-resistant leukemia.

18. The method of claim 17, wherein the drug-resistant leukemia is resistant to a FLT3 kinase inhibitor.

19. The method of claim 18, wherein the drug-resistant leukemia is resistant to PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, or CHIR-258.

20. The method of claim 17, wherein the mammal with the drug-resistant leukemia has a constitutively activating FLT3 mutant.

21. The method of claim 1, further comprising administering to the subject a therapeutically effective amount of a second therapeutic agent.

22. The method of claim 21, wherein the second therapeutic agent is an anticancer agent.

23. The method of claim 22, wherein the anticancer agent is selected from the group consisting of adriamycin, busulfan, cytarabine, cyclophosphamide, dexamethasone, fludarabine, fluorouracil, hydroxyurea, interferons, oblimersen, platinum derivatives, taxol, topotecan, and vincristine.

24. The method of claim 22, wherein the anticancer agent is a FLT3 kinase inhibitor selected from the group consisting of PKC 412, MLN 578, CEP-701, CT 53518, CT-53608, CT-52923, D-64406, D-65476, AGL-2033, AG1295, AG1296, KN-1022, PKC-412, SU5416, SU5614, SU11248, L-00021649, and CHIR-258.

25. The method of claim 1, further comprising a diagnostic step for determining the presence of a constitutively activating FLT3 mutant.

26. The method of claim 1, wherein the proliferative disease is a bladder cancer, breast cancer, cervical cancer, CNS cancer, colon cancer, esophageal cancer, head and neck cancer, liver cancer, lung cancer, nasopharyngeal cancer, neuroendocrine cancer, ovarian cancer, pancreatic cancer, prostate cancer, renal cancer, salivary gland cancer, small cell lung cancer, skin cancer, stomach cancer, testicular cancer, thyroid cancer, uterine cancer, or hematologic malignancy.

27. The method of claim 1, wherein the administration is oral.

28. The method of claim 1, wherein the administration is parenteral.

29. The method of claim 1, wherein the administration is intravenous.

30. The method of claim 1, wherein the dose is 12, about 18, about 27, about 40, about 60, about 90, about 135, about 200, or about 450 mg per day.

31. The method of claim 1, wherein the compound, or a pharmaceutically acceptable salt, or solvate thereof, is administered once per day for one week, two weeks, or three weeks.

32. The method of claim 31, wherein the compound, or a pharmaceutically acceptable salt, or solvate thereof, is administered once per day for fourteen days.

33. The method of claim 31, wherein the administration is followed by a rest period, during which the compound of Formula I is not administered.

34. The method of claim 33, wherein the rest period is one, two, three, four, five, six, or seven days; two, three, or four weeks.

35. The method of claim 1, wherein the mammal has not been treated with anticancer therapy for the proliferative disease prior to the administration of the compound of Formula I, or a pharmaceutically acceptable salt, solvate, or hydrate thereof.

36. The method of claim 1, wherein the mammal has been treated with anticancer therapy for the proliferative disease prior to the administration of the compound of Formula I, or a pharmaceutically acceptable salt, solvate, or hydrate thereof.

37. A pharmaceutical composition comprising a compound of Formula I:

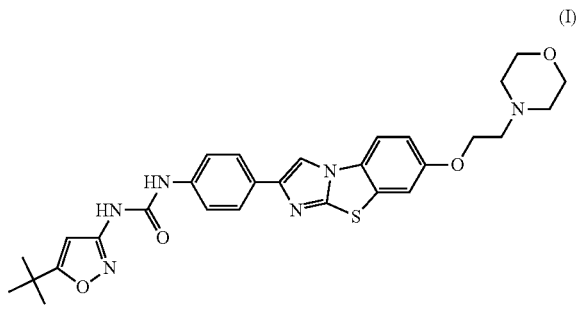

(I)

or a pharmaceutically acceptable salt or solvate thereof, and one or more pharmaceutically acceptable carriers selected from the group consisting of hydroxypropyl-β-cyclodextrin, mannitol, sodium starch glycolate, citric acid, PEG400, PEG6000, polyvinylpyrrolidone, lauroyl polyoxylglycerides, a block copolymer of ethylene oxide and propylene oxide, silicone dioxide, and water.

38. The pharmaceutical composition of claim 37, wherein the pharmaceutically acceptable carrier is lauroyl polyoxylglycerides.

39. The pharmaceutical composition of claim 37, wherein the pharmaceutically acceptable carrier is hydroxypropyl-β-cyclodextrin.

40. The pharmaceutical composition of claim 39, wherein the pharmaceutically composition is powder.

41. The pharmaceutical composition of claim 37, wherein the composition is formulated as a capsule.

42. The pharmaceutical composition of claim 37, wherein the compound is a dihydrochloride salt.

43. The pharmaceutical composition of claim 37, wherein the composition is formulated for single dose administration.

44. The pharmaceutical composition of claim 37, wherein the composition is formulated for oral administration.

45. The pharmaceutical composition of claim 40, wherein the powder is spray dried powder.

* * * * *